(12) United States Patent
Mucke et al.

(10) Patent No.: US 7,297,836 B2
(45) Date of Patent: Nov. 20, 2007

(54) METHODS OF DETECTING NEUROLOGICAL DISORDERS

(75) Inventors: Lennart Mucke, San Francisco, CA (US); Jorge J. Palop, San Francisco, CA (US)

(73) Assignee: The J. David Gladstone Institutes, Irvine, CA (US)

( * ) Notice: Subject to any disclaimer, the term of this patent is extended or adjusted under 35 U.S.C. 154(b) by 0 days.

(21) Appl. No.: 10/809,777

(22) Filed: Mar. 24, 2004

(65) Prior Publication Data
US 2004/0229258 A1 Nov. 18, 2004

Related U.S. Application Data

(60) Provisional application No. 60/457,200, filed on Mar. 24, 2003.

(51) Int. Cl.
G01N 33/00 (2006.01)
C12N 15/00 (2006.01)
(52) U.S. Cl. .............................. 800/3; 800/21
(58) Field of Classification Search ................. None
See application file for complete search history.

(56) References Cited

FOREIGN PATENT DOCUMENTS
WO    WO 96/40896    12/1996

OTHER PUBLICATIONS

Ristevski S, Making better transgenic models, 2005, Molecular Biotechnology, vol. 29, pp. 153-163.*
Smith KR, Gene transfer in higher animals: theoretical considerations and key concepts, J. of Biotechnology, vol. 99, pp. 1-22.*
Houdebine LM, The methods to generate transgenic animals and to control transgene expression, 2002, J. of Biotechnology, vol. 98, pp. 145-160.*
Montoliu L, Gene transfer strategies in animal transgenesis, 2002, Cloning and Stem Cells, vol. 4, pp. 39-46.*
Palop JJ, Neuronal depletion of calcium-dependent proteins in the dentate gyrus is tightly lined to Alzheimer's disease-relate cognitive deficits, 2003, PNAS, vol. 100, pp. 9572-9577.*
Mucke L, High-level neuronal expression of abeta 1-42 in wild-type human amyloid protein precursor transgenic mice: synaptotoxicity without plaque formation, 2000, J. of Neuroscience, vol. 20, pp. 4050-4058.*
Vezzani A, Seizure susceptibility and epileptogenesis are decreased in transgenic rats overexpressing neuropeptide Y, 2002, Neuroscience, vol. 110, pp. 237-243.*
Lamb L, Altered metabolism of familial Alzheimer's disease-linked amyloid precursor protein variants in yeast artificial chromosome transgenic mice, 1997, Human Molecular Genetics, vol. 6, pp. 1535-1541.*
Palop et al. (2003) *Proc. Natl. Acad. Sci. USA* 100:9572-9577.
Barski et al. (2003) *J. Neuroscience* 23:3469-3477.
Moechars et al. (1999) *J. Biol. Chem.* 274(10):6483-6492.
Mikkonen et al. (1999) *Neuroscience* 92(2):515-32.
Ichimiya, et al. (1998) *Brain Res.* 475, 156-159.
Hof, P. R. & Morrison, J. H. (1991) *Exp. Neurol.* 111, 293-301.
Baimbridge KG, et al. (1992) Trends Neurosci 15: 303-308.
Crabbe et al. (1999) *Science* 284:1670-1672.
Wahlsten et al. (2003) *J. Neurobiol.* 54:283-311.
Vig PJS, et al. (2001) Brain Res. Bull. 56:221-225.
Thoms V, et al, Neuropathology. Sep. 2001;21(3):203-11.
Potier B, et al. (1994) Brain Res 661:181-188.
Pasti L, et al. (1999) Neuroreport 10:2367-2372.
Nägerl UV, et al. (2000) J Neurosci 20:1831-1836.
Nägerl UV, and Mody I (1998) J Physiol 509:39-45.
Mucke L, et al. (2000) J Neurosci 20:4050-4058.
Molinari S, et al. (1996) Proc Natl Acad Sci USA 93:8028-8033.
Magloczky Z, et al. (1997) Neuroscience 76:377-385.
Lledo P-M, et al. (1992) Neuron 9:943-954.
Klapstein GJ, et al. (1998) Neuroscience 85:361-373.
Iritani S, et al, Neuropathology. Sep. 2001;21(3):162-7.
Iacopino AM, and Christakos S (1990) Proc Natl Acad Sci USA 87:4078-4082.
Hsia A, et al. (1999) Proc Natl Acad Sci USA 96:3228-3233.
Heyser CJ, et al. (1997) Proc Natl Acad Sci USA 94:1500-1505.
Heizmann CW, and Hunziker W (1991) Trends Biochem Sci 16:98-103.
Guo Q, et al. (1998) Proc Natl Acad Sci USA 95:3227-3232.
Greene JRT, et al. (2001) Neuropathol Appl Neurobiol 27:339-342.
Geula C, et al. (2003) JCompNeurol 455:249-259.
German DC, et al. (1997) Neuroscience 81:735-743.
Chard PS, et al. (1995) Proc Natl Acad Sci USA 92:5144-5148.
Palop et al. "Immunochemical indicators of neuronal and behavioral deficits in transgenic models of Alzheimer's Disease," Abstract 919 (Jul. 20-25, 2002) The 8th International Conference on Alzheimer's Disease and Related Disorders, Stockholm, Sweden.
West, M. J., Coleman, P. D., Flood, D. G. & Troncoso, J. C. (1994) *Lancet* 344, 769-772.
Dineley K T et al "Beta-amyloid activates the mitogen-activqated protein kinase cascade via hippocampal a7 nicotinic acetylcholine receptors: In vitro and In vivo mechanisms related to Alzheimer's disease" Journal of Neuroscience, New York, NY, vol. 21, No. 12, Jun. 15, 2001, pp. 4125-4133.
Echeverria Valentina et al. "Intracellular A-beta amloid, a sign for worse things to come?" Jul. 31, 1998, Molecular Neurobiology, vol. 26, Nr. 2-3, pp. 299-316.
Berrige, Michael J. "Neuronal calcium signaling" Jul. 1998, Neuron, vol. 21, NR 1, pp. 13-26.
Allen, et al. Elevation of Neuropeptide Y (NPY) in Substania Innominata in Alzheimer's Type Dementia. J. Neurolog. Sciences, 1984, 64, pp. 325-331.
Chan-Palay et al. II "Cortical neurons immunoreactive with antisera against Neuropeptide Y are altered in Alzheimer's-Type Dementia" J. comparative Neurology, 1985, 238, pp. 390-300.
Minthon et al. Cerebrospinal fluid Neuropeptide Y-like Immunoreactive levels in Demential of Alzheimer Type and Dementia with Frontotemporal Degeneration of Non-Alzheimer Type. Demntia, 1990 1 pp. 262-266.

* cited by examiner

*Primary Examiner*—Deborah Crouch
*Assistant Examiner*—David Montanari
(74) *Attorney, Agent, or Firm*—Carol L. Francis; Paula A. Borden; Bozicevic Field & Francis LLP

(57) ABSTRACT

The present invention provides methods of detecting an amyloid peptide-related neurological disorder in an individual; and methods for staging an amyloid peptide-related neurological disorder in an individual. The methods involve detecting a level of a calcium-responsive gene product, such as calbindin, in a hippocampal neuron, especially a granule cell of the dentate gyrus. The invention further provides identifying an agent that treats an amyloid peptide-related neurological disorder, as well as agents identified by the methods.

10 Claims, 13 Drawing Sheets

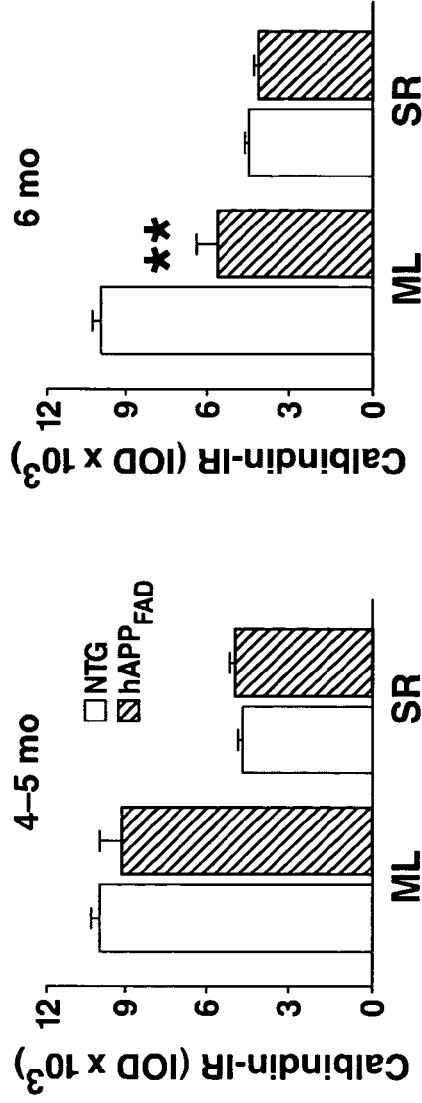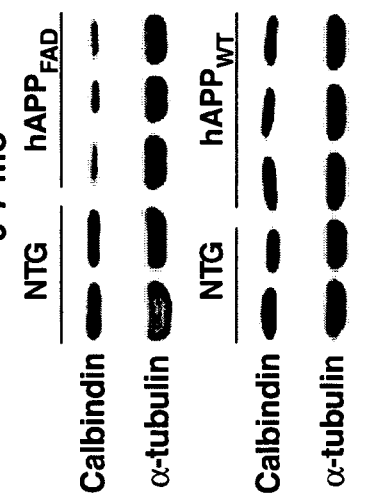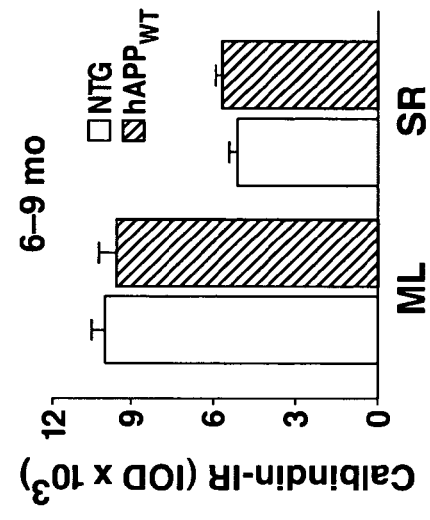

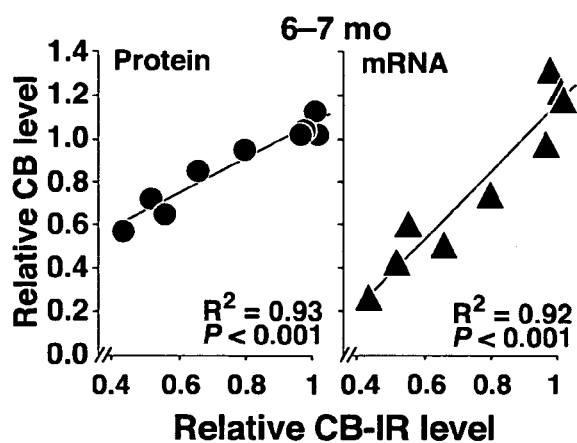
FIG. 1D
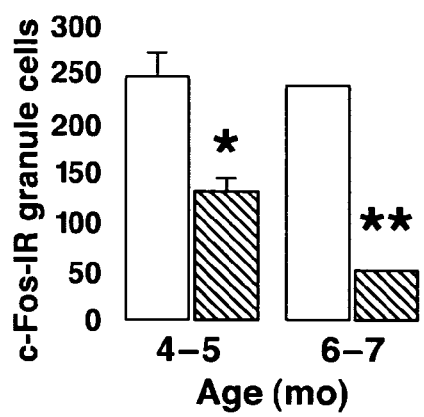
FIG. 1E
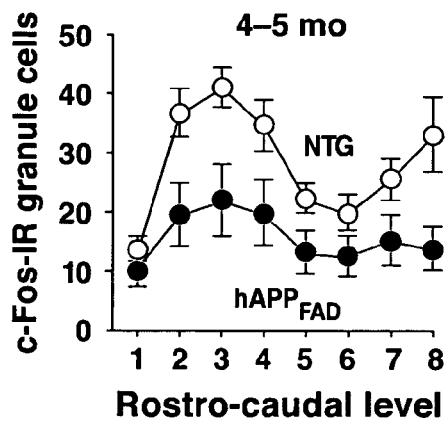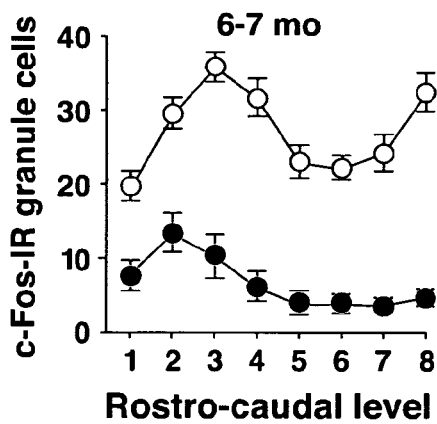
FIG. 1F

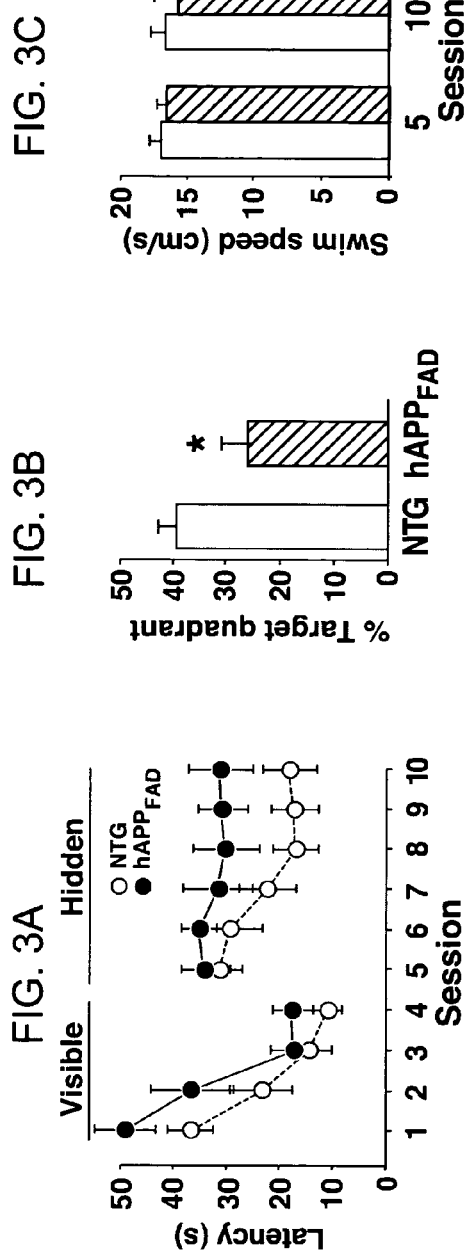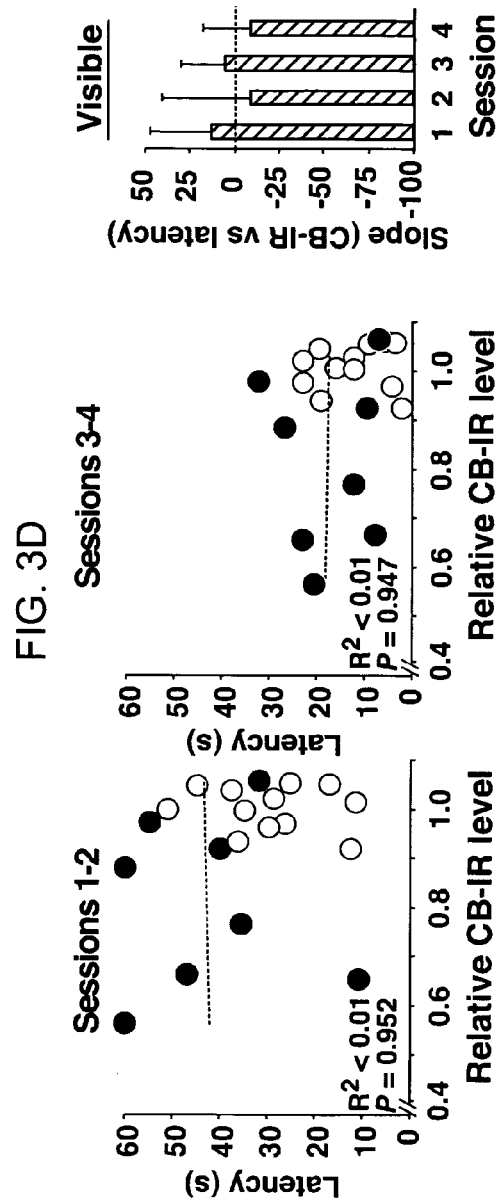

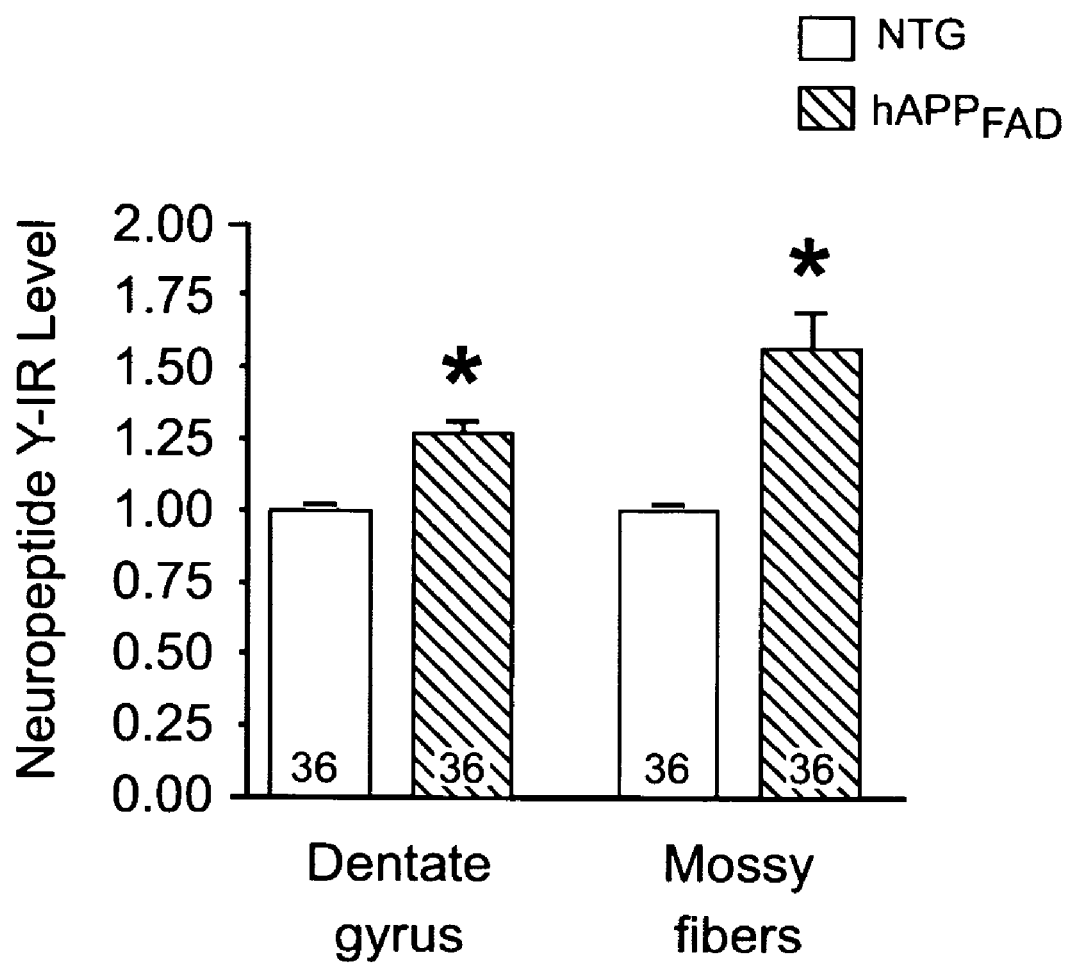

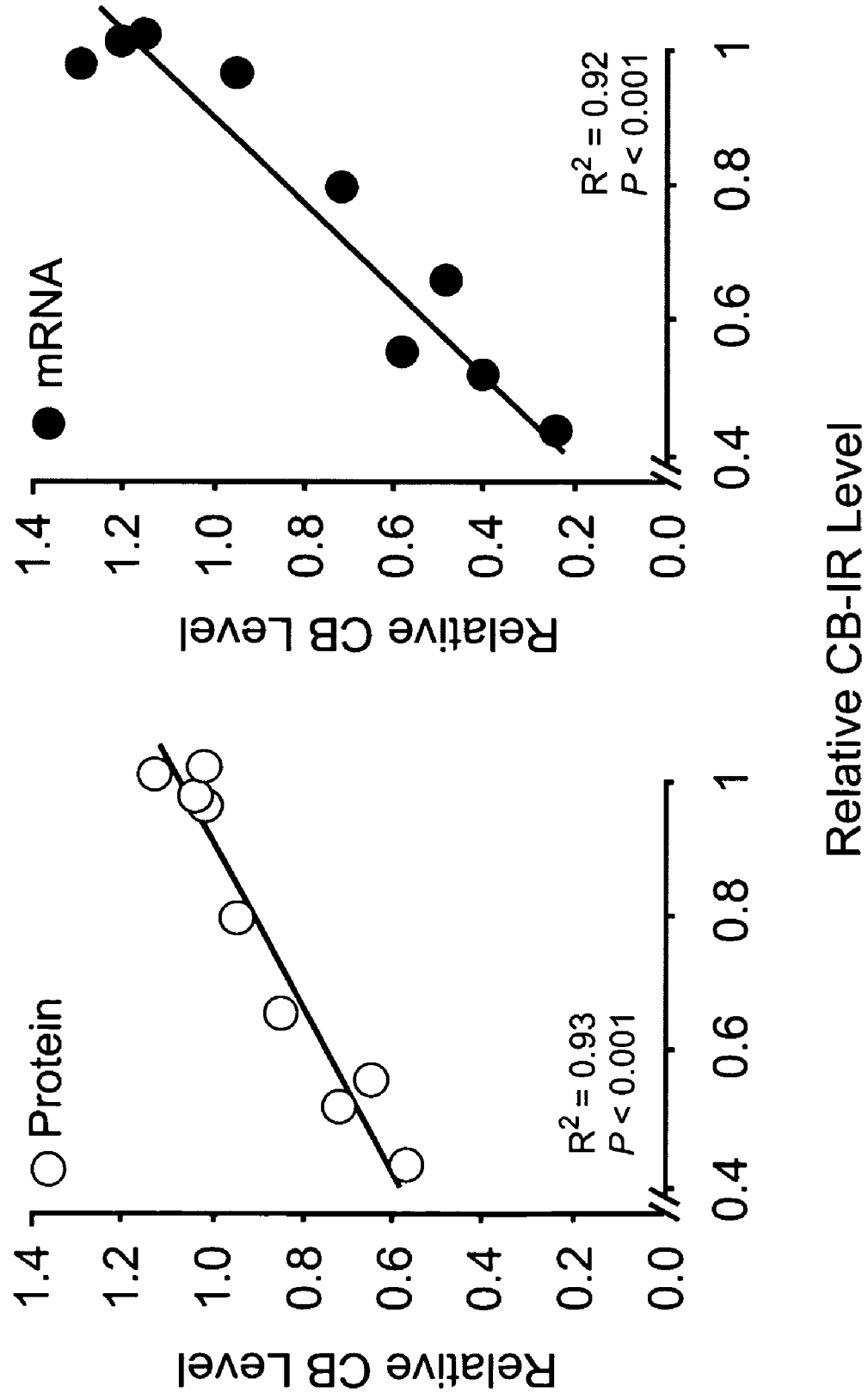

METHODS OF DETECTING NEUROLOGICAL DISORDERS

CROSS-REFERENCE

This application claims the benefit of U.S. Provisional Patent Application No. 60/457,200 filed Mar. 24, 2003, which application is incorporated herein by reference in its entirety.

STATEMENT REGARDING FEDERALLY SPONSORED RESEARCH

The U.S. government may have certain rights in this invention, pursuant to grant nos. AG11385, NS41787, and NS43945 awarded by the National Institutes of Health.

FIELD OF THE INVENTION

This application is in the field of cognitive impairment, and in particular Alzheimer's disease, cerebral amyloidosis, proteopathies of the aging central nervous system, and neurodegenerative disorders.

BACKGROUND OF THE INVENTION

The bright prospects of increasing life expectancy in many populations around the world are tempered by an alarming increase in amyloid peptide-related neurodegenerative disorders. Alzheimer's disease, the most frequent among these conditions, causes an inexorable loss of memory and other cognitive functions. Although the etiology of most AD cases remains elusive, several key features of this disease can be simulated in transgenic mice, making them amenable to experimental analysis and manipulation. Indeed, hAPP mice are used increasingly to assess novel AD treatments. Amyloid plaques have remained the primary pathological outcome measure in these studies, although their contribution to AD-related cognitive deficits is controversial. In fact, it remains to be determined which of the many pathological and biochemical alterations identified in AD and related transgenic models contribute most critically to the decline in neuronal functions.

Currently, mouse models of amyloid peptide-related neurological disorders such as Alzheimer's Disease are used for identifying agents that are useful for treating such disorders. The efficacy of a given test agent is typically determined by assessing and scoring behavioral traits such as learning and memory. An example of such a test is the water maze test. Such tests are time-consuming, may be somewhat subjective, and are subject to a high degree of variability and imprecision.

There is a need in the art for improved methods of detecting neurological disorders associated with neurotoxic levels of amyloid peptide. The present invention addresses this need, and provides an alternative read-out for efficacy of a test agent on treating cognitive impairment.

Literature

Palop et al. (2003) *Proc. Natl. Acad. Sci. USA* 100:9572-9577; Barski et al. (2003) *J. Neuroscience* 23:3469-3477; Greene et al. (2001) *Neuropathol. Applied Neurobiol.* 27:339-342; Thorns et al. (2001) *Neuropathol.* 21:203-211; Iritani et al. (2001) *Neuropathol.* 21:162-167; Palop et al. "Immunochemical indicators of neuronal and behavioral deficits in transgenic models of Alzheimer's Disease," Abstract 919 (Jul. 20-25, 2002) The 8th International Conference on Alzheimer's Disease and Related Disorders, Stockholm, Sweden; Heyser et al. (1997) *Proc. Nat'l. Acad. Sci. USA* 94:1500-1505; Moechars et al. (1999) *J. Biol. Chem.* 274(10):6483-6492; Mikkonen et al. (1999) *Neuroscience* 92(2):515-32; Ichimiya, et al. (1998) *Brain Res.* 475, 156-159; Hof, P. R. & Morrison, J. H. (1991) *Exp. Neurol.* 111, 293-301; West, M. J., Coleman, P. D., Flood, D. G. & Troncoso, J. C. (1994) *Lancet* 344, 769-772; Crabbe et al. (1999) *Science* 284:1670-1672; Wahlsten et al. (2003) *J. Neurobiol.* 54:283-311. Baimbridge K G, et al. (1992) Trends Neurosci 15:303-308; Celio M R (1990) Neuroscience 35:375-475; Chard P S, et al. (1995) Proc Natl Acad Sci USA 92:5144-5148; German D C, et al. (1997) Neuroscience 81:735-743; Geula C, et al. (2003) J Comp Neurol 455:249-259; Greene J R T, et al. (2001) Neuropathol Appl Neurobiol 27:339-342; Guo Q, et al. (1998) Proc Natl Acad Sci USA 95:3227-3232; Heizmann C W, and Hunziker W (1991) Trends Biochem Sci 16:98-103; Heyser C J, et al. (1997) Proc Natl Acad Sci USA 94:1500-1505; Hof P R, and Morrison J H (1991). Exp Neurol 111:293-301; Hsia A, et al. (1999) Proc Natl Acad Sci USA 96:3228-3233; Iacopino A M, and Christakos S (1990) Proc Natl Acad Sci USA 87:4078-4082; Iritani S, et al, Neuropathology. September 2001; 21(3):162-7; Klapstein G J, et al. (1998) Neuroscience 85:361-373; Lledo P-M, et al. (1992) Neuron 9:943-954; Magloczky Z, et al. (1997) Neuroscience 76:377-385; Mikkonen M, et al. (1999) Neuroscience 92:515-532; Molinari S, et al. (1996) Proc Natl Acad Sci USA 93:8028-8033; Mucke L, et al. (2000) J Neurosci 20:4050-4058; Nägerl U V, and Mody 1 (1998) J Physiol 509:39-45; Nägerl U V, et al. (2000) J Neurosci 20:1831-1836; Pasti L, et al. (1999) Neuroreport 10:2367-2372; Potier B, et al. (1994) Brain Res 661:181-188; Thorns V, et al, Neuropathology. September 2001; 21(3):203-11; Vig P J S, et al. (2001) Brain Res. Bull. 56:221-225.

SUMMARY OF THE INVENTION

The present invention provides methods of detecting an amyloid peptide-related neurological disorder in an individual; and methods for staging an amyloid peptide-related neurological disorder in an individual. The methods involve detecting a level of a calcium-responsive gene product, such as calbindin, in a hippocampal neuron, especially a granule cell of the dentate gyrus. The invention further provides identifying an agent that treats an amyloid peptide-related neurological disorder, as well as agents identified by the methods.

BRIEF DESCRIPTION OF THE DRAWINGS

FIGS. 1A-F depict results showing that calbindin and c-Fos reductions in the dentate gyrus depend on age and type of hAPP expressed.

FIGS. 3A-I depict results showing that reductions in calbindin and c-Fos correlate tightly with behavioral deficits.

FIG. 4 depicts ectopic expression of neuropeptide Y (NPY) in mossy fibers, and aberrant NPY/GABAergic sprouting in the molecular layer in hAPP$_{FAD}$ mice.

FIG. 10 depicts the correlation of reductions in calbindin immunoreactivity (IR) with reductions in calbindin protein and mRNA in hAPP$_{FAD}$ mice.

DEFINITIONS

Figure 2A:
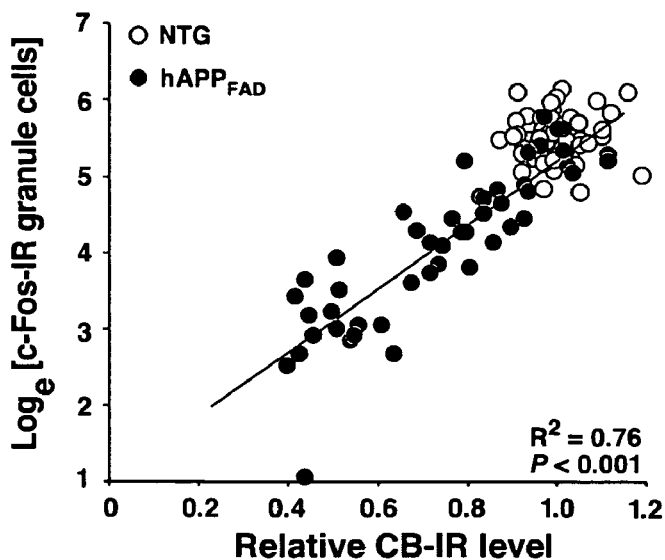
FIGS. 2A-C depict the relationship between calbindin, c-Fos, plaque load, and Aβ levels.

The term "amyloid peptide-related neurological disorder," as used herein, refers to any disorder that results from, or is associated with, accumulation of neurotoxic levels of amyloid peptides in the central nervous system, and/or formation of neurotoxic amyloid protein assemblies in the central nervous system. Such disorders include, but are not limited to, AD, Parkinson's disease, and Lewy body disease. The term includes cognitive impairments associated with AD, including impairment of learning ability, and memory impairment.

The term "Alzheimer's disease" (abbreviated herein as "AD") as used herein refers to a condition associated with formation of neuritic plaques comprising amyloid β protein, as well as impairment in both learning and memory. "AD" as used herein is meant to encompass both AD as well as AD-type pathologies and clinical manifestations.

The terms "calcium-responsive gene product," and "calcium-dependent gene product," as used interchangeably herein, refer to a protein and/or an mRNA whose level varies with the intracellular calcium ion concentration ($[Ca^{2+}]_i$). Calcium-responsive gene products include products of genes that include a calcium-responsive transcriptional regulatory element; calcium-binding proteins (e.g., calbindin); neuropeptide Y (NPY); an α-actinin II gene product; a phospho-extracellular signal-regulated kinase (phospho-ERK or p-ERK) gene product; immediate early response genes (e.g., c-Fos); and the like.

As used herein, the terms "determining," "measuring," and "assessing," and "assaying" are used interchangeably and include both quantitative and qualitative determinations.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The term "binds specifically," in the context of antibody binding, refers to high avidity and/or high affinity binding of an antibody to a specific polypeptide i.e., epitope of a polypeptide, e.g., a calcium-responsive polypeptide, such as a calbindin polypeptide or a c-Fos polypeptide. For example, antibody binding to an epitope on a specific calbindin polypeptide or fragment thereof is stronger than binding of the same antibody to any other epitope, particularly those which may be present in molecules in association with, or in the same sample, as the specific polypeptide of interest, e.g., binds more strongly to a specific calbindin epitope than to a different calbindin epitope so that by adjusting binding conditions the antibody binds almost exclusively to the specific calbindin epitope and not to any other calbindin epitope, and not to any other calbindin polypeptide (or fragment) or any other polypeptide which does not comprise the epitope. Antibodies which bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a subject polypeptide, e.g. by use of appropriate controls. In general, specific antibodies bind to a given polypeptide with a binding affinity of $10^{-7}$ M or more, e.g., 10-8 M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

The terms "treatment" "treating" and the like are used herein to refer to any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise.

Thus, for example, reference to "a granule cell" includes a plurality of such cells and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of detecting an amyloid peptide-related neurological disorder in an individual; and methods for staging an amyloid peptide-related neurological disorder in an individual. The methods involve detecting the level of a calcium-responsive gene product (e.g., calbindin) in a granule cell of the dentate gyrus in an individual. The invention further provides identifying an agent that treats an amyloid peptide-related neurological disorder. The invention further provides methods of modulating levels of a calcium-responsive gene product, such as calbindin, in a granule cell of the dentate gyrus in an individual.

The present invention is based on the observation that reduced calbindin levels and reduced c-Fos levels in hippocampal neurons, particularly cells of the dentate gyrus, are correlated with cognitive impairment, and with the relative abundance of hippocampal $A\beta_{1-42}$ among $A\beta$ peptides. Transgenic non-human animals, such as $A\beta$ transgenic mice, are used to identify agents that are useful for treating amyloid peptide-related disorders such as Alzheimer's Disease (AD). The efficacy of a given test agent is typically determined by assessing and scoring behavioral traits. Such tests are time-consuming and imprecise. Furthermore, many drugs are assessed using plaque formation as an outcome measure instead of behavioral testing. Because there is increasing evidence that plaque-independent neuronal deficits also appear to play a critical role in AD, measuring plaque formation may fail to identify drugs that might prevent or ameliorate plaque-independent neuronal deficits.

Amyloid plaques do not correlate well with cognitive impairment and other behavioral deficits associated with neurological disorders such as AD. Indeed, some amyloid protein does not form plaques, but instead forms small, neurotoxic assemblies that are not deposited as plaques. However, calbindin levels do correlate with the level and neurotoxic activity of amyloid protein, as well as with plaque-independent cognitive decline, and therefore provide a reliable marker for amyloid protein related neurological disorders.

The present invention provides an alternative read-out for the efficacy of a test agent on treating cognitive impairment. Because reduced calbindin levels in hippocampal neurons, such as the granule cells of the dentate gyrus, are correlated with cognitive impairment, the level of calbindin, as well as other calcium-dependent proteins, in these cells serves as a surrogate marker for behavioral characteristics. Calbindin levels can be quantitated. Quantitation allows a more precise analysis of the extent of the disease, and provides a measure of the degree of efficacy of a given test agent. The present invention provides for a readout of clinically relevant impairments, and thus presents a major advantage over the assessment of drugs by behavioral testing or by plaque quantitation.

Detection Methods

The present invention provides methods of detecting an amyloid peptide-related neurological disorder in an individual, or in a biological sample derived from an individual. The methods generally involve detecting a level of a calcium-responsive gene product in a hippocampal neuron in an individual, or in a biological sample derived from an individual. In many embodiments, calcium-responsive gene product levels are detected in the dentate gyrus, and in particular, a granule cell of the dentate gyrus.

Any of a number of calcium-responsive gene products can be detected in a granule cell of the dentate gyrus in a method of the present invention. Illustrative examples include calbindin, $\alpha$-actinin II, phospho-ERK, c-Fos, and neuropeptide Y. Those skilled in the art can readily apply such methods to other calcium-responsive gene products.

In some embodiments, a level of a calcium-dependent gene product in the dentate gyrus of an individual that is lower than the normal level of the gene product in the dentate gyrus indicates the presence of a neurological disorder in the individual (particularly, an amyloid peptide-related neurological disorder). Examples of calcium-dependent gene products that are lower in the dentate gyrus of an individual having an amyloid peptide-related neurological disorder include calbindin, p-ERK, $\alpha$-actinin II, and c-Fos. Thus, e.g., a level of a calcium-dependent gene product (e.g., calbindin, p-ERK, $\alpha$-actinin II, and c-Fos) that is at least about 10%, at least about 20%, at least about 30%, at least about 40%, at least about 50%, at least about 60%, at least about 70%, or at least about 80%, or more, lower than the normal level of that gene product in the dentate gyrus indicates that the individual has an amyloid peptide-related neurological disorder.

In other embodiments, a level of a calcium-dependent gene product in the dentate gyrus of an individual that is higher than the normal level of the gene product in the dentate gyrus indicates the presence of a neurological disorder in the individual (particularly, an amyloid peptide-related neurological disorder). Examples of calcium-dependent gene products that are higher in the dentate gyrus of an individual having an amyloid peptide-related neurological disorder include neuropeptide Y (NPY). Thus, e.g., a level of a calcium-dependent gene product (e.g., NPY) that is at least about 10%, at least about 20%, at least about 30%, at least about 40%, at least about 50%, at least about 60%, at least about 70%, at least about 80%, at least about 90%, at least about 100% (or two-fold), at least about 2.5-fold, at least about 3-fold, at least about 4-fold, or at least about 5-fold, (or greater) higher than the normal level of that gene product in the dentate gyrus indicates that the individual has an amyloid peptide-related neurological disorder.

Detecting Polypeptide Levels

In some embodiments, the methods involve detecting a calcium-responsive protein and/or mRNA level (e.g., calbindin protein and/or mRNA level) in a hippocampal neuron (e.g., a granule cell of the dentate gyrus) in vitro. Any method of detecting a calcium-responsive protein level (e.g., a calbindin protein level) in an in vitro biological sample can be used in conjunction with a subject method. Suitable methods of detecting a protein include, but are not limited to, protein blotting methods, enzyme linked immunosorbent assays, radioimmunoassays, and immunohistochemical methods. For example, a hippocampal brain section is contacted with an antibody that binds calbindin specifically, where the antibody is detectably labeled, either directly or indirectly.

Direct and indirect antibody labels are known in the art. An antibody may be labeled with a radioisotope, an enzyme, a fluorescer (e.g., a fluorescent protein or a fluorescent dye), a chemiluminescer, or other label for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

Fluorescent proteins include, but are not limited to, a green fluorescent protein (GFP), e.g., a GFP derived from *Aequoria Victoria* or a derivative thereof; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973; and the like.

Enzyme labels include, but are not limited to, luciferase, β-galactosidase, horse radish peroxidase, luciferase, alkaline phosphatase, and the like. Where the label is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

In some embodiments, the level of a calcium-responsive protein, such as calbindin, is quantitated. Methods of quantitating protein levels are known in the art. For example, enzyme-linked immunosorbent assay (ELISA) can provide for quantitation of calbindin levels. Calbindin levels in immunostained brain tissue sections can be quantitated by determining the integrated optical density of the immunoreactivity of an immunostained brain section, as described in the Example.

In other embodiments, a level of a calcium-dependent protein selected from calbindin, neuropeptide Y (NPY), α-actinin II, phospho-ERK (p-ERK), and c-Fos, is detected. Levels of proteins such as calbindin, neuropeptide Y (NPY), α-actinin II, phospho-ERK (p-ERK), and c-Fos are readily detected using well-known methods, including immunological assays. For example, p-ERK polypeptide levels are readily detected using a chemiluminescence enzyme immunometric assay (TiterZyme® CLIA; Assay Designs, Inc., Ann Arbor, Mich.), involving use of a p-ERK-specific IgG antibody, and an alkaline phosphatase-labeled IgG-specific antibody. NPY, and methods for detecting NPY, are well described in the literature. See, e.g., Erickson et al. (1996) *Nature* 381:415; and Minth et al. (1984) *Proc. Natl. Acad. Sci. USA* 81:4577. Alpha-actinin-II is well described in the literature. See, e.g., Wyszynski et al. (1998) *J. Neurosci.* 18:1383. Phospho-ERK is well described in the literature. See, e.g., Li et al. (2001) *Neurobiol. Dis.* 8:127; and Fahlman et al. (2002) *Brain Res.* 958:43-51.

In many embodiments, the detection method is an in vitro detection method involving detecting a calcium-responsive gene product, e.g., a calbindin level, in a granule cell of the dentate gyrus in a brain sample from a transgenic non-human animal model of a neurodegenerative disorder. Transgenic non-human animal models of Alzheimer's disease are well known in the art. For example, various non-human animal models of neurodegenerative disorders such as AD are described in, e.g., U.S. Pat. Nos. 5,767,337; 6,046,381; 6,175,057; and 6,455,757; and Mucke et al. (2000) *J. Neurosci.* 20:4050-4058; Masliah et al. (2001) *Proc. Natl. Acad. Sci. USA* 98:12245-12250; and Rockenstein et al. (1995) *J. Biol. Chem.* 270:28257-25267. Non-limiting examples of suitable animal models include hAPP transgenic mice that express high levels of hAPP; and hAPP transgenic mice that express low levels of hAPP and that are also transgenic for fyn kinase. In these embodiments, a hippocampal brain sample is taken from a transgenic non-human animal model of a neurodegenerative disorder, and the level of a calcium-dependent protein and/or a calcium-dependent protein-encoding mRNA is detected in the dentate gyrus.

Detecting mRNA Levels

Where the calcium-responsive gene product is an mRNA (e.g., a calbindin mRNA, an NPY mRNA, a c-Fos mRNA, an α-actinin II mRNA, a p-ERK mRNA, and the like), any of a variety of known methods for detecting an mRNA can be used. In general, nucleic acids that hybridize specifically to a calcium-responsive mRNA, e.g., a calbindin mRNA, are used. A number of methods are available for analyzing nucleic acids for the presence and/or level of a specific mRNA in a cell or in a sample. The mRNA may be assayed directly or reverse transcribed into cDNA for analysis. Suitable methods include, but are not limited to, in situ nucleic acid hybridization methods, quantitative reverse transcription-polymerase chain reaction (RT-PCR), nucleic acid blotting methods, and the like.

The nucleic acid may be amplified by conventional techniques, such as the polymerase chain reaction (PCR), to provide sufficient amounts for analysis. The mRNA may be reverse transcribed, then subjected to PCR (rtPCR). The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2-14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMPA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546;

Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

In some embodiments, calbindin mRNA levels (and/or a NPY mRNA level, a c-Fos mRNA level, an α-actinin II mRNA level, a p-ERK mRNA level) are quantitated using quantitative rtPCR. Methods of quantitating a given message using rtPCR are known in the art. In some of these embodiments, dye-labeled primers are used. In other embodiments, a double-stranded DNA-binding dye, such as SYBR®, is used, as described in the Examples. Quantitative fluorogenic RT-PCR assays are well known in the art, and can be used in the present methods to detect a level of calbindin mRNA. See, e.g., Pinzani et al. (2001) *Regul. Pept.* 99:79-86; and Yin et al. (2001) *Immunol. Cell Biol.* 79:213-221.

Other examples of calcium-responsive gene products that are suitable for detection using a method of the present invention is immediate early gene products such as c-Fos and Arc. Thus, in some embodiments, the method involves detecting a level of c-Fos protein in the hippocampus, e.g., in a granule cell of the dentate gyrus. As discussed in the Example, a reduced level of c-Fos in hippocampal neurons correlates with behavioral deficits, such as cognitive impairment, associated with AD. Thus, in some embodiments, the methods involve detecting a level of c-Fos protein and/or mRNA in a sample. In many embodiments, c-Fos levels are detected in a granule cell of the dentate gyrus. A level of c-Fos polypeptide is detected by employing immunological methods as described above, using antibody specific for c-Fos.

Alternatively, c-Fos mRNA is detected, using nucleic acids that hybridize specifically to c-Fos nucleic acids. A number of methods are available for analyzing nucleic acids for the presence and/or level of a specific mRNA in a cell, as described above. The mRNA may be assayed directly or reverse transcribed into cDNA for analysis.

The level of a calcium-responsive gene product in an animal model of an amyloid peptide-related neurodegenerative disorder is compared to the level of the calcium-responsive gene product in control animals, e.g., animals of the same species that are not models for the disorder. For example, where the animal model is a non-human animal transgenic for a neurodegeneration-promoting protein such as $A\beta_{1-42}$, suitable controls are wild-type, e.g., not transgenic for the neurodegeneration-promoting protein. For example, where the animal is a transgenic hAPP animal, a non-transgenic animal of the same species serves as a control. Typically, the test animal and the control animal are the same sex.

While not required, validation of the method may be carried out by detecting a level of $A\beta_{1-42}$ protein in the hippocampus (e.g., in a granule cell of the dentate gyrus), and correlating a level of calbindin in the hippocampus (e.g., granule cell of the dentate gyrus) with the level of $A\beta_{1-42}$ protein in the hippocampus. $A\beta_{1-42}$ levels are measured using standard immunological methods, as described above, using antibody specific for $A\beta_{1-42}$.

In some embodiments, detection of calcium-responsive gene product levels in granule cells of the dentate gyrus is carried out in vivo in a living subject, including a living mouse model of an amyloid peptide-related neurological disorder, and a living human subject. Thus, the present invention provides methods for antemortem detection of calcium-responsive gene product levels, e.g., calbindin levels, in granule cells of the dentate gyrus. In some embodiments, the methods involve administering to a living subject a detectably labeled compound that specifically binds the calcium-responsive gene product, and detecting binding between the detectably labeled compound and the calcium-responsive gene product in a granule cell of the dentate gyrus. In other embodiments, the methods involve administering to a living subject a detectably labeled agent that binds a factor that decreases along with a decrease in calcium-responsive gene product levels; and detecting binding between the agent and the factor. Suitable detection methods include, but are not limited to, magnetic resonance imaging (MRI), positron emission tomography, single photon emission computed tomography, functional MRI, and the like.

In other embodiments, detection of calcium-responsive gene product level in granule cells of the dentate gyrus is carried out postmortem on a biological sample of a human subject. Detection of calcium-responsive gene product levels is carried out as described above, e.g., by detecting calbindin and/or mRNA levels in a dentate gyrus sample taken from a deceased human subject.

Detecting Multiple Calcium-Dependent Gene Products

In some embodiments, two or more calcium-responsive gene products are detected. As one non-limiting example, in some embodiments, both calbindin protein levels and c-Fos protein levels are detected. Thus, in some embodiments, a subject method involves detecting a level of calbindin protein in a brain sample, and detecting a level of c-Fos protein in the brain sample, e.g., in granule cells of the dentate gyrus. In other embodiments, two or more polypeptides selected from a calbindin polypeptide, an NPY polypeptide, a c-Fos polypeptide, a p-ERK polypeptide, and an α-actinin II polypeptide are detected in the brain sample, e.g., in granule cells of the dentate gyrus. Thus, in some embodiments, a subject method involves detecting a level of two or more proteins selected from a calbindin polypeptide, an NPY polypeptide, a c-Fos polypeptide, a p-ERK polypeptide, and an α-actinin II polypeptide in a brain sample, e.g., in granule cells of the dentate gyrus.

In other embodiments, both calbindin mRNA and c-Fos mRNA levels are detected. Thus, in some embodiments, a subject method involves detecting a level of calbindin mRNA in a brain sample, and detecting a level of c-Fos mRNA in the brain sample, e.g., in granule cells of the dentate gyrus. In other embodiments, two or more mRNAs selected from a calbindin mRNA, an NPY mRNA, a c-Fos mRNA, a p-ERK mRNA, and an α-actinin II mRNA are detected. Thus, in some embodiments, a subject method involves detecting a level of two or more mRNAs selected from a calbindin mRNA, an NPY mRNA, a c-Fos mRNA, a p-ERK mRNA, and an α-actinin II mRNA.

Screening Methods

The invention provides methods of identifying agents that improve cognition; methods of identifying agents that increase a level of a calcium-responsive gene product (e.g., calbindin, α-actinin II, p-ERK, c-Fos) in a hippocampal neuron in an individual; methods of identifying agents that block the effect of amyloid peptide on neurons; methods of identifying agents that reduce the level of abnormal amyloid assemblies; methods of identifying agents that increase clearance of amyloid peptides, and methods of identifying agents that decrease neurotoxic levels of amyloid peptides.

The methods generally involve administering a test agent to a transgenic non-human animal model of a neurodegenerative disorder, where the test agent contacts a hippocampal neuron (e.g., a granule cell of the dentate gyrus); and detecting a level of calcium-responsive gene product (e.g., calbindin, α-actinin II, p-ERK, c-Fos, NPY, etc.) in vitro in brain tissue of the animal. Detection of a level of a calcium-dependent gene product in the brain tissue that is significantly different from a level of the calcium-responsive gene product in the absence of the agent indicates that the test agent modulates a level of the calcium-responsive gene product in the brain tissue of the animal.

In general, a test agent that effects an increase or a decrease in a hippocampal neuron calcium-responsive gene product level (e.g., a calbindin level in a granule cell of the dentate gyrus), such that the increase or decrease is toward a normal level of the gene product, is a candidate agent for treating a cognitive impairment. For example, a test agent that effects an increase in a calbinding, an α-actinin II, or a p-ERK gene product in the dentate gyrus is a candidate agent for treating a cognitive impairment (e.g., an amyloid peptide-related cognitive impairment). As another example, a test agent that increases a level of an NPY gene product in the dentate gyrus is a candidate agent for treating a cognitive impairment (e.g., an amyloid peptide-related cognitive impairment). In many embodiments, the method provides for identification of agents that modulate a cognitive impairment in the animal. In particular embodiments, the level of a calcium-dependent gene product, e.g., a calcium-dependent gene product selected from a calbindin gene product, an α-actinin II gene product, an NPY gene product, and a p-ERK gene product, in a granule cell of the dentate gyrus is detected.

Test Agents

The terms "candidate agent," "test agent," "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Candidate agents are generally small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Screening may be directed to known pharmacologically active compounds and chemical analogs thereof, or to new agents with unknown properties such as those created through rational drug design.

Assays of the invention include controls, where suitable controls include a control animal (e.g., an animal of the same genotype) not administered with the test agent. In some embodiments, a plurality of assays is run in parallel with different agent concentrations to obtain a differential response to the various concentrations. Typically, one of these concentrations serves as a negative control, i.e. at zero concentration or below the level of detection.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

In some embodiments, e.g., where the level of the calcium-dependent gene product is reduced in the dentate gyrus of an individual having an amyloid peptide-related neurological disorder (including cognitive impairment), a test agent that effects an increase in a hippocampal neuron level of a calcium-responsive gene product (e.g., an agent that effects an increase in a calbindin level), particularly an increase in a level of a calcium-responsive gene product in a granule cell of the dentate gyrus, is a candidate agent for treating a cognitive impairment. A test agent that effects an increase in a hippocampal neuron calcium-responsive gene product level (e.g., a calbindin level in a granule cell of the dentate gyrus) by at least about 5%, at least about 10%, at least about 15%, at least about 20%, at least about 25%, at least about 30%, at least about 35%, at least about 40%, at least about 45%, at least about 50%, or more, compared to the level in a hippocampal neuron (e.g., granule cell of the dentate gyrus) not contacted with the test agent, indicates that the test agent is a candidate agent for treating an amyloid peptide-related cognitive impairment.

In other embodiments, e.g., where the level of the calcium-dependent gene product is increased in the dentate gyrus of an individual having an amyloid peptide-related neurological disorder (including cognitive impairment), a test agent that effects a decrease in a hippocampal neuron level of a calcium-responsive gene product (e.g., an agent that effects a reduction in an NPY gene product level), particularly a reduction in a level of a calcium-responsive gene product in a granule cell of the dentate gyrus, is a candidate agent for treating a cognitive impairment. A test agent that effects a reduction in a hippocampal neuron calcium-responsive gene product level (e.g., an NPY level in a granule cell of the dentate gyrus) by at least about 5%, at least about 10%, at least about 15%, at least about 20%, at least about 25%, at least about 30%, at least about 35%, at least about 40%, at least about 45%, or at least about 50%, or more, compared to the level in a hippocampal neuron (e.g., granule cell of the dentate gyrus) not contacted with the test agent, indicates that the test agent is a candidate agent for treating an amyloid peptide-related cognitive impairment.

Administration

A test agent is administered in vivo to a transgenic non-human animal model of a neurodegenerative disorder, where the test agent contacts a hippocampal neuron. Transgenic non-human animal models of amyloid peptide-related neurodegenerative disorders are well known in the art. For example, various non-human animal models of neurodegenerative disorders are described in, e.g., U.S. Pat. Nos. 5,767,337; 6,046,381; 6,175,057; and 6,455,757; and Mucke et al. (2000) *J. Neurosci.* 20:4050-4058; Masliah et al. (2001) *Proc. Natl. Acad. Sci. USA* 98:12245-12250; and Rockenstein et al. (1995) *J. Biol. Chem.* 270:28257-25267.

The test agent is administered by any convenient route of administration, including, but not limited to, intragastric, intracranial, intramuscular, intravenous, topical, subcutaneous, intratracheal, and the like.

In some embodiments, a subject screening method provides for determining whether a test agent crosses the blood brain barrier. For example, a test agent that is effective in increasing hippocampal neuron calcium-responsive gene product levels when administered intracranially is modified in vitro and the derivatives thus formed are administered to the animal intravenously. If the agent is effective when administered intravenously, then it likely crosses the blood brain barrier. Various modifications to a test agent, e.g., acetylations, acylations, phophorylations, and the like, can be tested in this manner.

In vitro Screening

After the animal is administered with the test agent, the level of calcium-responsive gene product (e.g., a protein and/or mRNA selected from calbindin, α-actinin II, c-Fos, NPY, and p-ERK) in brain tissue of the animal is detected in an in vitro assay. In vitro screening is conducted following administration of the test agent, e.g., usually after a period of about 10 minutes, about 15 minutes, about 30 minutes, about 60 minutes, about 2 hours, about 4 hours, or more, following administration of the test agent.

Typically, a hippocampal brain sample is taken from the animal, and calcium-responsive protein (e.g., calbindin) is detected. In many embodiments, the brain sample is a dentate gyrus sample. Samples derived from an animal model of amyloid peptide-related cognitive impairment are used in assays. Typically, samples are hippocampal samples, e.g., dissociated hippocampal neurons, hippocampal brain sections, and the like. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

As described below, in some embodiments, a level of calcium-responsive protein in a hippocampal brain sample is detected. In some embodiments, a level of calbindin protein is detected. In other embodiments, a level of c-Fos protein in a hippocampal neuron is detected. Where a level of c-Fos protein is detected, the methods discussed for detecting calbindin protein are used, except that an antibody specific for c-Fos is employed.

As described below, in some embodiments, a level of calcium-responsive mRNA in a hippocampal brain sample is detected. In some of these embodiments, a level of calbindin mRNA is detected in the hippocampal brain sample. Alternatively, a level of c-Fos mRNA is detected.

Detecting Calcium-Responsive Proteins

In many embodiments, an antibody specific for a given calcium-responsive polypeptide is used. As one non-limiting example, a calbindin level is detected, and an antibody specific for calbindin is used. The antibody is detectably labeled, either directly or indirectly. Various labels include radioisotopes, fluorescers, chemiluminescers, enzymes, specific binding molecules (e.g., members of specific binding pairs), particles, e.g. magnetic particles, and the like. Specific binding molecules include pairs, such as biotin and streptavidin, digoxin and antidigoxin, lectin and carbohydrate, antibody and antigen, antibody and hapten, etc. For the specific binding members, the complementary member would normally be labeled with a molecule that provides for detection, in accordance with known procedures. Direct and indirect antibody labels are known in the art. An antibody may be labeled with a radioisotope, an enzyme, a fluorescer (e.g., a fluorescent protein or a fluorescent dye), a chemiluminescer, or other label for direct detection. Alternatively, a second stage antibody or reagent is used to amplify the signal. Such reagents are well known in the art, and are discussed above.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, anti-microbial agents, etc. may be used. The mixture of components is added in any order that provides for the requisite binding (e.g., of antibody to calbindin in the sample). Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

Detection of calcium-responsive protein (e.g., calbindin) may utilize staining of cells or histological sections, performed in accordance with conventional methods. The antibodies of interest are added to the cell sample or brain section sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method depends on the in vitro detection of binding between antibodies and calcium-responsive protein (e.g., calbindin) in a cell lysate. Measuring binding between an antibody and a protein in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

Detecting c-Fos

In some embodiments, a level of c-Fos in a brain tissue is also detected in an in vitro assay. Methods for detecting c-Fos are described above. In some of these embodiments, a test agent that effects an increase in both a hippocampal neuron calbindin level and a hippocampal c-Fos level is a candidate agent for treating a cognitive impairment. A test agent that effects an increase in a hippocampal neuron calbindin level by at least about 5%, at least about 10%, at least about 15%, at least about 20%, at least about 25%, at least about 30%, at least about 35%, at least about 40%, at least about 45%, at least about 50%, or more, and that effects an effects an increase in a hippocampal neuron c-Fos level by at least about 5%, at least about 10%, at least about 15%, at least about 20%, at least about 25%, at least about 30%, at least about 35%, at least about 40%, at least about 45%, at least about 50%, or more compared to the calbindin and c-Fos levels in a hippocampal neuron not contacted with the test agent, indicates that the test agent is a candidate agent for treating an amyloid peptide-related neurodegenerative disorder, such as cognitive impairment. In particular embodiments, the level of calbindin in a granule cell of the dentate gyrus is detected.

Therapeutic Agents

The invention provides agents identified using the methods described herein. Agents that increase a level of a calcium-responsive gene product (e.g., calbindin, α-actinin-II, p-ERK), where the level of the gene product is decreased in the dentate gyrus in a neuropathology, are used to treat amyloid peptide-related neurological disorders, particularly cognitive impairment. Agents that reduce a level of a calcium-dependent gene product (e.g., NPY), where the level of the gene product is increased in the dentate gyrus under neuropathological conditions, are use to treat amyloid peptide-related neurological disorders, particularly cognitive impairment. An effective amount of the active agent is administered to the host, where "effective amount" means a dosage sufficient to produce a desired result. Generally, the desired result is at least an amelioration of at least one neuropathological symptom (e.g., at least a reduction in a learning deficit) as compared to a control.

Formulations

In the subject methods, the active agent(s) may be administered to the host using any convenient means capable of resulting in the desired reduction in any amyloid peptide-related neurological disorder, particularly amyloid peptide-related cognitive impairment.

Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that increases a level of calcium-responsive gene product in a hippocampal neuron (e.g., a granule cell of the dentate gyrus) and can be administered in a single dose. Alternatively, a target dosage of an agent that increases a level of calbindin in a hippocampal neuron can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that increases a level of calcium-responsive gene product in a granule cell of the dentate gyrus is administered to an individual using any available method and route suitable for drug delivery, including in vivo and ex vivo methods, as well as systemic and localized routes of administration.

Conventional and pharmaceutically acceptable routes of administration include intranasal, intramuscular, intracranial, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intracranial, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a behavioral deficit associated with AD. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Crossing the Blood-Brain Barrier

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the central nervous system (CNS) may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) Fed. Proc. 43:214-219; Baba et al. (1991) J. Cereb. Blood Flow Metab. 11:638-643; and Gennuso et al. (1993) Cancer Invest. 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) J. Med. Chem. 23:682-684; Pardridge (1991) in: Peptide Drug Delivery to the Brain; and Kostis et al. (1994) J. Clin. Pharmacol. 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, α-cyclodextrin, β-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (mAb) to the specific carrier molecule transferrin receptor, which facilitated the uptake of the VIPa-mAb conjugate through the blood-brain barrier. Pardridge (1991); and Bickel et al. (1993) Proc. Natl. Acad Sci. USA 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Subjects Suitable for Treatment

Subjects suitable for treatment with a subject agent include those having any amyloid peptide-related neurodegenerative disorders. Subjects suitable for treatment with a subject agent include individuals diagnosed as having AD or probable AD. Subjects suitable for treatment includes those exhibiting AD-related cognitive impairments and/or genetic, imaging, or biochemical evidence indicating that they are at increased risk of developing such deficits. Also suitable for treatment are individuals who are at increased risk of developing AD (e.g., individuals with two apoE4 alleles).

Utility

The instant methods are useful for detecting an amyloid peptide-related neurological disorder (e.g., AD); for determining the severity of an amyloid peptide-related neurological disorder; for monitoring the progression of an amyloid peptide-related disorder; for monitoring the response of an individual to a drug for treating an amyloid peptide-related disorder; and for identifying pathways and molecular manipulations that affect AD-type pathology in animal models of AD.

The instant methods are useful for diagnosing an amyloid peptide-related neurological disorder in a non-human animal model of amyloid peptide-related neurological disorders. Thus, e.g., a reduction in hippocampal (especially dentate gyrus) calbindin levels (and/or α-actinin-II levels, and/or p-ERK levels) of at least about 5%, at least about 10%, at least about 15%, at least about 20%, at least about 25%, at least about 30%, at least about 35%, at least about 40%, at least about 45%, at least about 50%, or more, compared with a control, is diagnostic for an amyloid peptide-related neurological disorder.

The instant methods are useful to assess the severity of an amyloid peptide-related neurological disorder in a non-human animal model of an amyloid peptide-related neurological disorder. The severity of an amyloid peptide-related neurological disorder can be assessed by comparing the detected levels of calbindin with levels of calbindin in samples, and associating the level with the severity of the amyloid peptide-related neurological disorder. In this embodiment, a relatively very low level of calbindin is usually associated with severe (i.e. highly progressed) amyloid peptide-related neurological disorder, a relatively low level of calbindin is usually associated with moderate amyloid peptide-related neurological disorder, and somewhat lower than normal level is usually associated with mild amyloid peptide-related neurological disorder. The severity of the disease may allow the selection of more efficacious therapies, for example a mild case of Alzheimer's disease may be more susceptible to certain drugs than a severe case.

The instant methods are also useful for monitoring the response to treatment with a drug in a non-human animal model of an amyloid peptide-related neurological disorder. For example, levels of dentate calbindin are detected in a non-human animal model of an amyloid peptide-related neurological disorder that is administered with a drug being tested for its efficacy in treating behavioral deficits associated with an amyloid peptide-related neurological disorder, such as AD. Increase in the levels of calbindin following treatment with a drug, relative to a control animal not treated with the drug, indicates that the drug treatment is effective in treating behavioral deficits.

The instant methods are also useful for in vivo detection methods in humans. In vivo detection of calbindin levels in dentate gyrus granule cells in humans are useful for diagnosis of an amyloid peptide-related neurodegenerative disorder, for staging of an amyloid peptide-related neurodegenerative disorder, and for assessing an individual's response to drug treatment for an amyloid peptide-related neurodegenerative disorder.

The instant methods are also useful for postmortem analysis of human biological samples, e.g., postmortem analysis of granule cells of the dentate gyrus. Such analyses are useful to stage a neurodegenerative disease, such as AD, and/or to assess the effectiveness of a given treatment for a neurodegenerative disease, such as AD, in a human subject.

The instant methods are also useful for identifying pathways and molecular manipulations that affect AD-type pathologies in animal models of AD.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s, second(s); min, minute(s); h or hr, hour(s); and the like.

Example 1

Correlation of Hippocampal Calbindin Levels with Relative Levels of $A\beta_{1-42}$ and with Cognitive Impairment Materials and Methods Animals and Behavioral Testing This study included 148 mice from line J20 (80 nontransgenic, 68 transgenic) and 57 mice from line I5 (25 nontransgenic, 33 transgenic), representing F6-F10 offspring from crosses of heterozygous transgenic mice with C57BL/6 nontransgenic breeders. Mucke et al. (2000) *J. Neurosci.* 20:4050-4058. Comparisons between transgenic and nontransgenic mice were performed on littermates. Mice had free access to food (Rodent Diet 20, PicoLab) and water. They were singly housed for 24 h before the behavioral testing and group housed otherwise. The light/dark cycle was 12 h with lights on at 6:00 a.m. Behavioral testing was carried out during the light cycle. Male mice were used for behavioral testing and female mice for Aβ measurements by ELISA. Other measurements were carried out on gender-balanced groups. No significant differences in calbindin, c-Fos-IR granule cells, and plaque load were identified between age- and genotype-matched male and female mice.

The water maze consisted of a pool (diameter, 122 cm) of opaque water (24° C.) with a platform (diameter, 10 cm) submerged 2.0 cm below the surface. For the cued training sessions, a white pen (length, 14.5 cm) with a red cap was mounted on the platform to indicate its location. The pen was removed for the hidden platform session. Mice were trained to locate first the visible platform (sessions 1-4) and then the hidden platform (sessions 5-10) in two daily sessions (3.5 h apart), each consisting of three 60-s trials (15-min intertrial interval). In the cued training, the location of the platform was changed with each session. In the hidden platform training, the platform location remained constant for each mouse. Mice were placed into the periphery of the pool and entry points were changed semirandomly between trials. Mice that failed to locate the platform were assigned an escape latency value of 60 s for that trial. Decreases in the average time (latency) and path length required to navigate to the platform in each session were used as putative measures of learning. One hour after completion of the hidden platform training, a 60-s probe trial (platform removed) was performed to determine whether mice spent more time in the quadrant where the platform was previously hidden (target quadrant) than in the other quadrants. Entry points for the probe trial were in the quadrant opposite to the target quadrant. The performance of the mice was monitored with an EthoVision video-tracking system (Noldus Instruments) set to analyze two samples per second.

For histological and biochemical analyses, mice were anesthetized with chloral hydrate and flush perfused transcardially with phosphate-buffered saline (PBS). Brains were removed and divided sagittally. For Aβ ELISAs, the hippocampus of one hemibrain was dissected on ice, immediately frozen on dry ice, and stored at −70° C. until analysis. The other hemibrain was postfixed in phosphate-buffered 4% paraformaldehyde, pH 7.4, at 4° C. for 48 h.

Human Brain Tissues

Human brain tissues were obtained postmortem from people examined neurologically and psychometrically (including Blessed score, Mini Mental State Examination, and dementia-rating scale) at the Alzheimer Disease Research Center of the University of California at San Diego within 12 months before death. Fifteen AD cases (9 females, ages 75-90 years (84.6±4.6, mean ±SD); 6 males, ages 71-92 years (82.2±9.2)) and two nondemented controls (1 female, age 74; 1 male, age 71) were included in this study. Neocortical, limbic, and subcortical tissues from each case were fixed in 10% buffered formalin, embedded and sectioned in paraffin, stained with haematoxylinleosin or with thioflavine-S, and analyzed by light microscopy to determine the extent of plaques and tangles and the Braak stage. Cases were divided into AD and nondemented controls following the diagnostic criteria of the Consortium to Establish a Registry for Alzheimer's disease (CERAD) and the National Institute on Aging (NIA). For immunohistochemical analyses, hippocampal tissues were postfixed for 72 h in 4% phosphate-buffered paraformaldehyde and serially sectioned with a vibratome.

Immunohistochemistry

Free-floating vibratome sections (50 μm) of mouse tissues were used for fluorescence double immunolabeling (calbindin and Neu-N) and free-floating freeze sliding microtome sections (30 μm) for single immunolabeling with the standard avidin-biotin/peroxidase method (calbindin, c-Fos, or Aβ). Free-floating vibratome sections (40 μm) of human tissues were used for calbindin immunoperoxidase staining. After quenching of endogenous peroxidase activity and blocking of nonspecific binding sites, sections were incubated overnight with primary antibodies in 3% preimmune serum from the species in which the secondary antibody was raised, 0.2% gelatin, and 0.5% Triton X-100 in PBS. The following primary antibodies were used: anti-calbindin (rabbit polyclonal, Swant, 1:15,000), anti-c-Fos (rabbit polyclonal Ab-5, Oncogene, 1:10,000), anti-Neu-N (mouse monoclonal, Chemicon International, 1:5,000), and anti-Aβ (mouse monoclonal 3D6, Elan Pharmaceuticals, 1:500). Secondary antibodies consisted of fluorescein-conjugated donkey anti-rabbit (Jackson ImmunoResearch, 1:300), Texas Red-conjugated donkey anti-mouse (Jackson ImmunoResearch, 1:300), biotinylated goat anti-rabbit (Vector Laboratories, 1:300), biotinylated goat anti-mouse (Vector Laboratories, 1:600), and biotinylated goat anti-rabbit (Vector Laboratories, 1:200). Diaminobenzidine was used as a chromagen in immunoperoxidase reactions. Immunofluorescence was visualized by confocal microscopy (Radiance 2000, BioRad) and immunoperoxidase staining by light microscopy.

Quantitation of Immunoreactive Structures

Digitized images of immunostained sections were obtained with a DEI-470 digital camera (Optronics) mounted on a BX-60 microscope (Olympus) at final magnifications of ×300 (calbindin), ×100 (c-Fos), and ×60 (Aβ). Calbindin levels were quantitated as follows. For each mouse, two coronal sections (300 μm apart) were selected between −2.54 and −2.80 mm from the bregma. The integrated optical density (IOD) of immunoreactivities was determined with the BioQuant Image Analysis package (R&M Biometrics) in two areas (0.04 $mm^2$ each) of the molecular layer of the dentate gyrus and two areas (0.04 $mm^2$ each) of the stratum radiatum of the CA1 region. These measurements were used to calculate average IODs for each brain region. Relative calbindin levels were expressed as the ratio of IOD readings obtained in the molecular layer and the stratum radiatum of the same section. The mean ratio obtained in nontransgenic controls was arbitrarily defined as 1.0.

Relative levels of c-Fos-IR granule cells were determined by counting all c-Fos-IR cells in the granular layer of the dentate gyrus in every tenth coronal section (serial sections, 30 μm thick) throughout the rostrocaudal extent of the granule cell layer. The average percent area of the hippocampus occupied by Aβ-immunoreactive deposits was determined in four coronal sections (300 μm apart) per mouse with the BioQuant Image Analysis package.

Western Blot and Quantitative Fluorogenic Reverse Transcriptase Polymerase Chain Reaction (qfRT-PCR) Analysis of Microdissected Dentate Gyrus Mice were anesthetized and flush perfused transcardially with RNase-free PBS. Hemibrains were dissected, immediately frozen on dry ice and stored at −70° C. To obtain tissue samples of the dentate gyrus, hemibrains were thawed on ice and sliced with a vibratome into 450-μm thick sagittal sections. From each section, the dentate gyrus was isolated on ice under a binocular microscope.

For protein quantifications, samples were immediately stored in 50% glycerol in PBS at −70° C. Samples of the dentate gyrus isolated from sagittal sections at comparable medial-lateral levels were individually sonicated three times (5 sec each) at 4° C. in lysis buffer containing 1 mM HEPES pH 7.4, 150 mM NaCl, 50 mM NaF, 1 mM EDTA, 1 mM DTT, 1 mM PMSF, 1 mM $Na_3VO_4$, and 10 μg/ml leupeptin, 10 μg/ml aprotinin, and 1% SDS. After incubation at 4° C. for 15 min, samples were centrifuged for 10 min at 5,000×g. Protein concentration was determined by Bradford assay and equal amounts of protein were loaded per lane, resolved by SDS-PAGE, and transferred to nitrocellulose membranes. After blocking in 5% nonfat dry milk in Tris-buffered saline/0.05% Tween 20, membranes were labeled with anti-calbindin (rabbit polyclonal, Swant, 1:20,000), anti-hAPP (mouse monoclonal 8E5, Elan Pharmaceuticals, 1:1,000), or anti-α-tubulin (mouse monoclonal B512, Sigma, 1:100,000), followed by incubation with HRP-conjugated goat anti-rabbit IgG (Chemicon, 1:5,000) or goat anti-mouse IgG (Chemicon, 1:10,000) secondary antibodies. Bands were visualized by ECL and quantitated densitometrically with Quant One 4.0 software (BioRad). Calbindin and hAPP levels were normalized to α-tubulin levels.

For mRNA quantification, total RNA was isolated and DNase treated with an RNeasy kit (Qiagen). RT reactions (Applied Biosystems) contained 120 ng total RNA and 2.5 μM each of random hexamer and oligo d(T) primers. After the RT reaction, samples were diluted 1:60 and analyzed by PCR with SYBR Green reagents (Molecular Probes) and an ABI Prism 7700 sequence detector (Applied Biosystems). Levels of calbindin, hAPP, and GAPDH cDNAs were determined relative to standard curves established with serial dilutions (1:3) of pooled cDNAs from all samples. The slopes of the standard curves were: calbindin −3.48, hAPP −3.51, and GAPDH −3.40. The purity of PCR products was confirmed with dissociation curves. No significant signal was detected when RT was omitted from reactions. Since GAPDH cDNA levels were comparable among genotypes, they were used to control for nonspecific variations in cDNA content among samples.

Primer sequences: calbindin (calbindin forward GGAAAGGAGCTGCAGAACTTGAT (SEQ ID NO:01); calbindin reverse TTCCGGTGATAGCTCCAATCC (SEQ ID NO:02)), c-Fos (c-Fos forward AACCTGGTGCTGGATTGTATCTAGT (SEQ ID NO:03); c-Fos reverse TTCTTAGTTTAATATTGGTCGTTTCTAATTG (SEQ ID NO:04)); GAPDH (GAPDH forward GGGAAGCCCATCACCATCTT (SEQ ID NO:05); GAPDH reverse GCCTTCTCCATGGTGGTGAA (SEQ ID NO:06)); and hAPP (hAPP forward GAGGAGGATGACTCGGATGTCT (SEQ ID NO:07); hAPP reverse AGCCACTTCTTCCTCCTCTGCTA (SEQ ID NO:08)).

Statistics

Statistical analyses were carried out with SPSS 10.0 program (SPSS, Chicago, Ill.). Unless indicated otherwise, quantitative data were expressed as mean ±SEM, and differences between means were assessed by unpaired two-tailed Student's t-test. Differences among means were evaluated by analysis of variance (ANOVA) and Tukey-Kramer posthoc test. Multiple stepwise linear regression was carried out for multivariate analysis. Age was included as an independent variable, and levels of soluble Aβ1-42, Aβ1-x, and plaque load were expressed in Log natural scale. $\alpha=0.05$ for all analyses.

Results

The relationship between morphological, biochemical, and behavioral alterations in transgenic mice, in which neuronal expression of hAPP is directed by the platelet-derived growth factor (PDGF) β chain promoter, was investigated. Mucke et al. (2000) *J. Neurosci.* 20:4050-4058.

Mice from line J20 express familial AD-mutant (K670N, M671L, V717F; hAPP770 numbering) hAPP (hAPP$_{FAD}$) and have high levels of human Aβ in the hippocampal formation, which includes the dentate gyrus and is critically involved in learning and memory. Mucke et al. (2000), supra. The expression of calcium-dependent proteins in these brain regions was analyzed. First, calbindin, a 28-kD calcium-binding protein that is particularly abundant in neurons of the dentate gyrus and highly responsive to alterations in calcium influx, was analyzed.

Most hAPP$_{FAD}$ mice had significantly lower neuronal calbindin levels in the dentate gyrus than nontransgenic controls (FIG. 1a). The calbindin reduction was most prominent in the granular layer, as well as in the molecular layer into which the granule cells extend their dendrites, whereas it did not notably affect the pyramidal cells in the CA1 region or their dendrites in the stratum radiatum of the hippocampus (FIG. 1a). Double-labeling of brain sections from hAPP$_{FAD}$ mice for calbindin and the neuronal marker Neu-N indicated that the calbindin reduction in the dentate gyrus primarily reflects a decrease in neuronal calbindin levels rather than a loss of calbindin-producing neurons.

Although loss of calbindin-positive neurons in cortical areas of AD cases has been observed previously, to the best of our knowledge, no studies have reported calbindin reductions in granule cells of the dentate gyrus in AD. In fact, granule cells are particularly resistant to AD-associated cell death. Yet, we found strong reductions in neuronal calbindin levels in the dentate gyrus of AD cases, with the most striking depletions seen in the most severely demented individuals. These results support the clinical relevance of the calbindin reductions we observed in hAPP$_{FAD}$ mice. They also demonstrate that neuronal populations resisting cell death in AD can still be drastically altered at the molecular level. Although many more cases will need to be analyzed to establish the extent to which calbindin reductions correlate with cognitive deficits in AD, it is tempting to speculate that such molecular alterations may have functional implications.

The calbindin reduction in hAPP$_{FAD}$ mice was age dependent in that it was highly significant at 6 months but barely notable at 4-5 months (FIG. 1a). PDGF-hAPP transgenic mice from line I5 (Mucke et al. (2000) supra) with neuronal expression of wildtype hAPP (hAPP$_{WT}$) showed no significant reductions in calbindin at 6-9 months (FIGS. 1b, 1c) or at 11-13 and 13-15 months (n=8-12 hAPP$_{WT}$ mice and n=5-11 nontransgenic controls per age group), suggesting that the prominent calbindin reductions in hAPP$_{FAD}$ mice are causally related to the FAD mutation and its pathophysiological consequences.

Reductions in calbindin immunoreactivity in 6-7-month-old hAPP$_{FAD}$ mice correlated tightly with calbindin protein and mRNA levels in the dentate gyrus of the opposite hemibrain (FIGS. 1c and 1d), indicating a mechanism affecting gene expression. Since calbindin expression is strongly influenced by calcium, we next examined the expression of the immediate early gene, c-fos, which is also critically dependent on calcium. The number of c-Fos immunoreactive (IR) neurons in the granule cell layer of the dentate gyrus was significantly reduced in hAPP$_{FAD}$ mice even at 4-5 months of age, and further decreases were observed by 6-7 months (FIGS. 1e, 1f). At the latter age, c-Fos reductions in hAPP$_{FAD}$ mice were significant at all rostrocaudal levels of the dentate gyrus analyzed (FIG. 1f).

FIGS. 1a-f. Calbindin and c-Fos reductions in the dentate gyrus depend on age and on the type of hAPP expressed. FIGS. 1a, 1b, Coronal brain sections were obtained from hAPP$_{FAD}$ mice of line J20 (a), hAPP$_{WT}$ mice of line I5 (b), and nontransgenic (NTG) littermate controls. Ages in months (mo) are indicated above each panel (n=10-13 mice per age and genotype). IOD, integrated optical density. ML, molecular layer. SR, stratum radiatum. Significant calbindin reductions in hAPP$_{FAD}$ mice were also detected at 6-7, 9-11, and 14-15 months (n=48 mice per age and genotype) but were not worse than those at 6 months of age (data not shown). FIGS. 1c, 1d, Total protein and RNA were extracted from dentate gyrus samples from hAPP$_{FAD}$ mice of line J20, hAPP$_{WT}$ mice of line I5, and nontransgenic controls. Levels of calbindin protein (c; d, left) and mRNA (d, right) were determined by western blot analysis and qfRT-PCR, respectively, and expressed as calbindin/α-tubulin (d, left) and calbindin/GAPDH (d, right) ratios. FIGS. 1e, 1f, Coronal brain sections from hAPP$_{FAD}$ mice of line J20 and nontransgenic controls (n=13-18 mice per age and genotype) were immunolabeled for c-Fos and the relative number of c-Fos-IR neurons in the granular layer was determined. Data represent group means for all sections analyzed (e) or for different rostrocaudal levels of the dentate gyrus (f). For all panels *P<0.05, **P<0.001.

In contrast to nontransgenic controls, hAPP$_{FAD}$ mice showed substantial interindividual variations in calbindin and c-Fos (FIG. 2a). However, calbindin and c-Fos reductions in hAPP$_{FAD}$ mice were tightly correlated (FIG. 2a), suggesting that the mechanisms underlying these variations are nonrandom and overlapping.

In the dentate gyrus of 6-7-month-old hAPP$_{FAD}$ mice (n=9), levels of calbindin (mRNA, protein, or IR) did not correlate with levels of hAPP$_{FAD}$ (mRNA or protein) (P>0.7 for all six calbindin-hAPP$_{FAD}$ correlations), suggesting that the calbindin reductions in hAPP$_{FAD}$ mice are not caused by the expression of hAPP$_{FAD}$ per se. To assess whether reductions in calbindin and c-Fos may be caused by Aβ, we analyzed their relationship with Aβ deposits (plaques), levels of soluble Aβ1-42 and Aβ1-x, and Aβ1-42/Aβ1-x ratios. Calbindin and c-Fos reductions in hAPP$_{FAD}$ mice did not correlate with the extent of Aβ deposition (FIG. 2b) but correlated strongly with the Aβ1-42/Aβ1-x ratio (FIG. 2c), which reflects the abundance of Aβ ending at residue 42 relative to other, mostly shorter, Aβ peptides.

These results are consistent with mounting evidence that AD-related neuronal deficits may be caused by nondeposited Aβ assemblies rather than by plaques. They are also consistent with studies suggesting that, above an absolute threshold concentration, the formation of neurotoxic Aβ assemblies depends more on relative than absolute levels of Aβ1-42. Although Aβ production is dependent on hAPP levels, the formation of neurotoxic Aβ assemblies may be strongly affected by proteins that bind or degrade Aβ. This may explain why reductions in calbindin and c-Fos correlated with the relative abundance of Aβ1-42 but not with hAPP$_{FAD}$ levels. The exact mechanisms by which Aβ assemblies may reduce calbindin and c-Fos levels remain to be determined. They could involve destabilization of the neuronal calcium homeostasis by chronic inflammation, formation of pores in cell membranes, and alterations in the function of calcium channels and other membrane proteins.

Figure 2B:
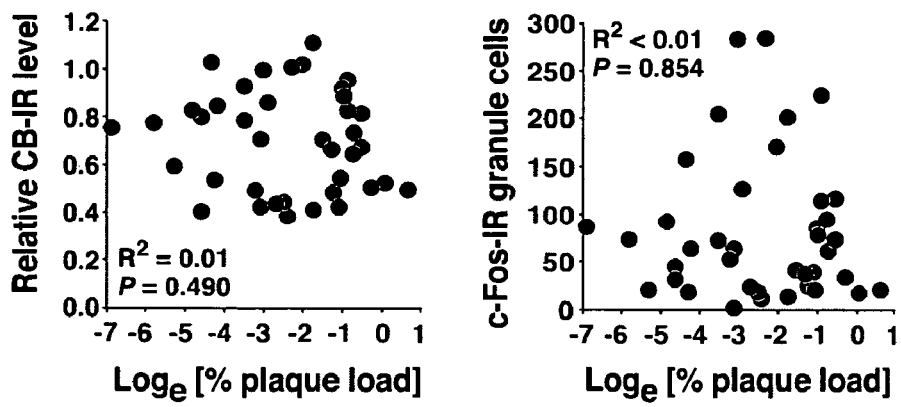
Figure 2C:
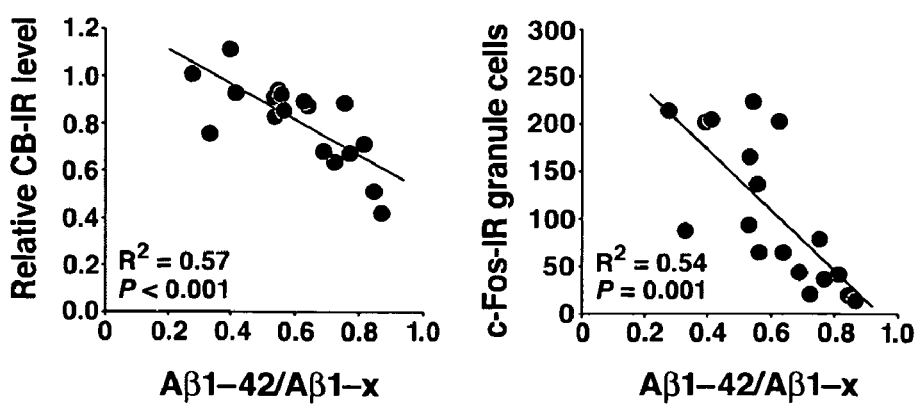

FIGS. 2a-c. Relationship between calbindin, c-Fos, plaque load, and Aβ levels. Brain sections and snap-frozen hippocampi were obtained from hAPP$_{FAD}$ mice from line J20 (FIGS. 2a-c) and nontransgenic controls (FIG. 2a). $R^2$ and P values refer to hAPP$_{FAD}$ mice only. FIG. 2a, Relative levels of calbindin and c-Fos-IR granule cells in the dentate gyrus were strongly correlated in hAPP$_{FAD}$ mice but not in nontransgenic controls (n=48-60 per genotype, age: 4-7 months). FIG. 2b, Neither calbindin nor c-Fos-IR granule cells correlated with hippocampal plaque load in hAPP$_{FAD}$ mice with early plaque formation (n=39, age: 4-7 months). FIG. 2c, Hippocampal levels of Aβ1-42 and Aβ1-x (approximates total Aβ) were determined in hAPP$_{FAD}$ mice (n=18) over a wider range of ages (4-22 months, mean ±SD: 10.7±6.7 months). The levels of calbindin and c-Fos-IR granule cells correlated inversely with Aβ1-42/Aβ1-x ratios, but not with plaque load (P>0.6).

To further assess the pathophysiological significance of calbindin and c-Fos reductions in hAPP$_{FAD}$ mice, we analyzed hAPP$_{FAD}$ mice and nontransgenic controls in a Morris water maze test, which provides putative measures of learning and memory. Behavioral deficits in hAPP$_{FAD}$ mice showed a striking relationship to neuronal reductions in calbindin and c-Fos (FIG. 3A-I).

The majority of hAPP$_{FAD}$ mice learned to navigate to a visible platform, demonstrating efficient cued learning (sessions 1-4), but showed significant deficits in the spatial component of the test, during which they had to use extra-maze cues to locate a hidden platform (sessions 5-10) (FIG. 3a). These hAPP$_{FAD}$ mice were also impaired in the probe trial (FIG. 3b), which provides a putative measure of memory retention. However, they did not differ from nontransgenic controls in swim speed (FIG. 3c), suggesting that their longer escape latencies during the hidden platform sessions were not due to motor deficits.

Figure 3E:
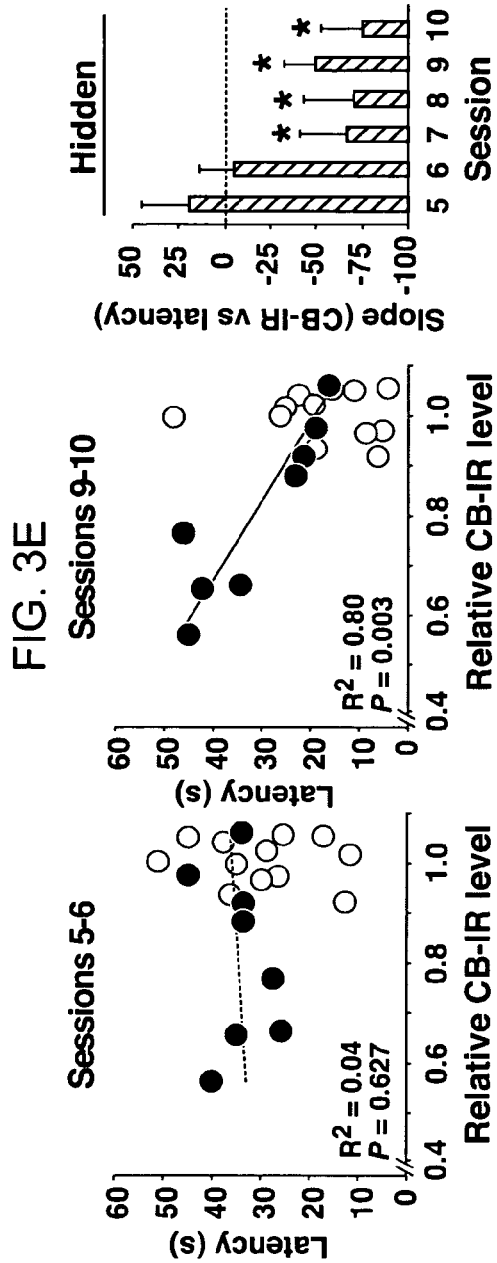
Figure 3F:
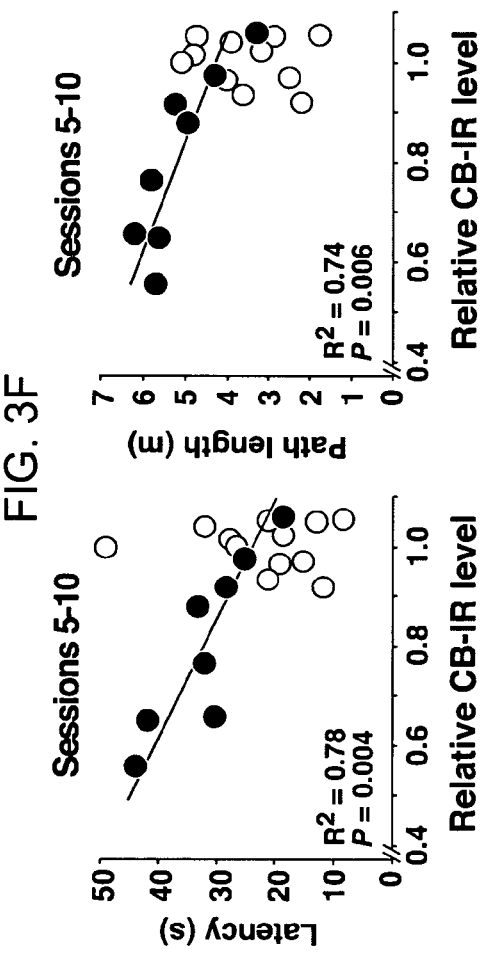

In nontransgenic controls and in hAPP$_{FAD}$ mice with deficits in spatial, but not cued, learning, calbindin levels in the dentate gyrus did not correlate with cued learning (FIG. 3d). Calbindin levels were also unrelated to the performance of hAPP$_{FAD}$ mice and nontransgenic controls in the first two sessions of the hidden platform training (FIG. 3e, sessions 5-6), before significant spatial learning was evident in the controls (FIG. 3a). However, in contrast to nontransgenic mice, hAPP$_{FAD}$ mice showed a tight correlation between calbindin levels and spatial learning deficits in the last four sessions of hidden platform training (FIG. 3e, sessions 7-10), when spatial learning was clearly occurring in control mice (FIG. 3a). This correlation remained strong when escape latencies and path lengths were averaged over all hidden platform trials (FIG. 3f). The relative level of c-Fos-IR granule cells also correlated strongly with spatial learning in hAPP$_{FAD}$ mice but not in nontransgenic controls (FIG. 3g).

Figure 3G:
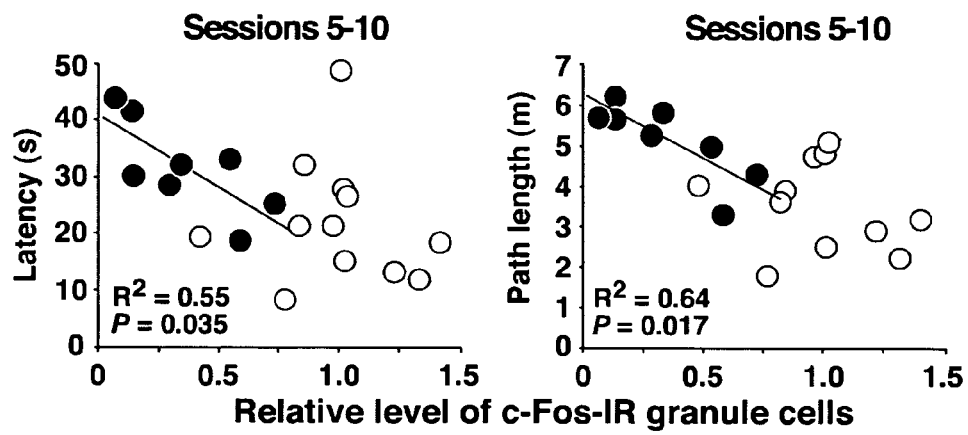
Figure 3H:
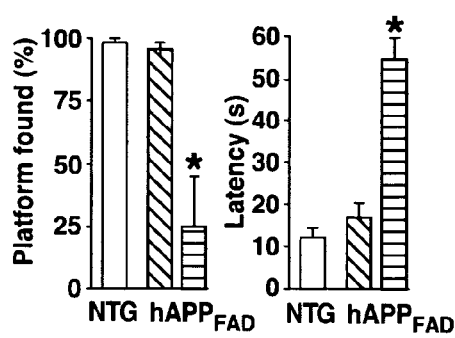
Figure 3I:
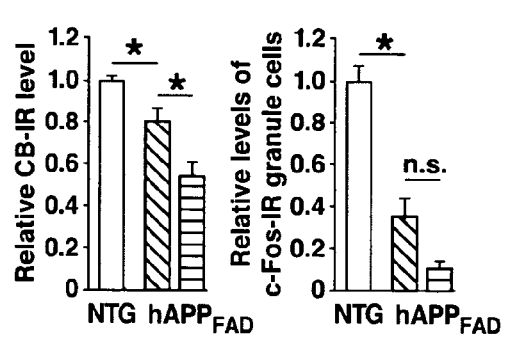

Some hAPP$_{FAD}$ mice were excluded from the above analysis of spatial learning because they had significant deficits even in cued learning (FIG. 3h). Interestingly, these mice also had the most prominent reductions in both calbindin and c-Fos-IR granule cells (FIG. 3i). The mechanisms underlying these severe behavioral impairments might differ from those causing more selective spatial learning deficits (FIG. 3a-g) quantitatively, qualitatively, or both. The visible and hidden platform components of the water maze test appear to involve overlapping cognitive functions, raising possibilities for extensions of deficits from one component to the other. While selective lesions of the hippocampal formation typically impair learning in the spatial, but not cued, component of the test, AD affects many brain regions besides the hippocampus combining spatial learning deficits with other cognitive impairments. Widespread neuronal expression of hAPP$_{FAD}$/Aβ may have similar effects in severely impaired transgenic mice.

FIGS. 3a-i. Reductions in calbindin and c-Fos correlate tightly with behavioral deficits. hAPP$_{FAD}$ mice from line J20 (black dots or columns) and nontransgenic littermate controls (empty dots or columns) (n=12 males per genotype, age: 6-7 months) were trained in a Morris water maze. After the behavioral testing, relative levels of calbindin and c-Fos-IR neurons in the dentate gyrus were measured. FIGS. 3a-c, Learning curves (FIG. 3a), probe trial performance (FIG. 3b), and average swim speeds (FIG. 3c) of nontransgenic controls (n=12) and of hAPP$_{FAD}$ mice (n=8) showing learning deficits when the platform was hidden but not when it was visible. Assessment of session effects in (FIG. 3a) by repeated measures ANOVA revealed that hAPP$_{FAD}$ mice learned the cued task (P<0.001) but not the spatial task (P>0.95), whereas nontransgenic controls learned both tasks (P<0.001). Average swim speeds in (FIG. 3c) were calculated for sessions 5 and 10 from all trials performed in the respective session. FIGS. 3d-e, Relationship of relative calbindin-IR levels and escape latencies during sessions in which the platform was visible (FIG. 3d) or hidden (FIG. 3e). See (FIG. 3a) for sequence of sessions. Dots represent mean latency values of individual mice calculated from the sessions indicated above each panel. Bars represent the slope coefficient "b" in the linear regression equation (y=a+bx) for hAPP$_{FAD}$ mice in the training sessions indicated. FIG. 3f, Correlation of relative calbindin levels with average escape latencies (left) and path lengths (right) calculated from all sessions of hidden platform training. Calbindin levels did not correlate with average swim speeds in the visible (P=0.86) or hidden (P=0.47) platform component of the test. FIG. 3g, Correlation of relative levels of c-Fos-IR granule cells with average escape latencies (left) and path lengths (right) calculated as in (FIG. 3f). The mean number of c-Fos-IR granule cells identified in nontransgenic controls was arbitrarily defined as 1.0. FIG. 3h, Four hAPP$_{FAD}$ mice (grey columns) were excluded from the above analysis because they showed a significant deficit in the visible platform training, defined here as an average latency (mean of all trials in sessions 3 and 4) exceeding the average latency plus two SD in nontransgenic controls. In contrast to the other mice, this group of hAPP$_{FAD}$ mice did not consistently find the visible platform, although they oriented normally to the investigator when allowed to exit the water maze (not shown). FIG. 3i, Relative levels of calbindin and c-Fos-IR granule cells in nontransgenic contols and hAPP$_{FAD}$ mice that did or did not show deficits in the visible platform training. *P<0.05. R$^2$ and P values in (FIGS. 3e-g) refer to hAPP$_{FAD}$ mice only; no significant correlations were identified in nontransgenic controls.

Figure 5:
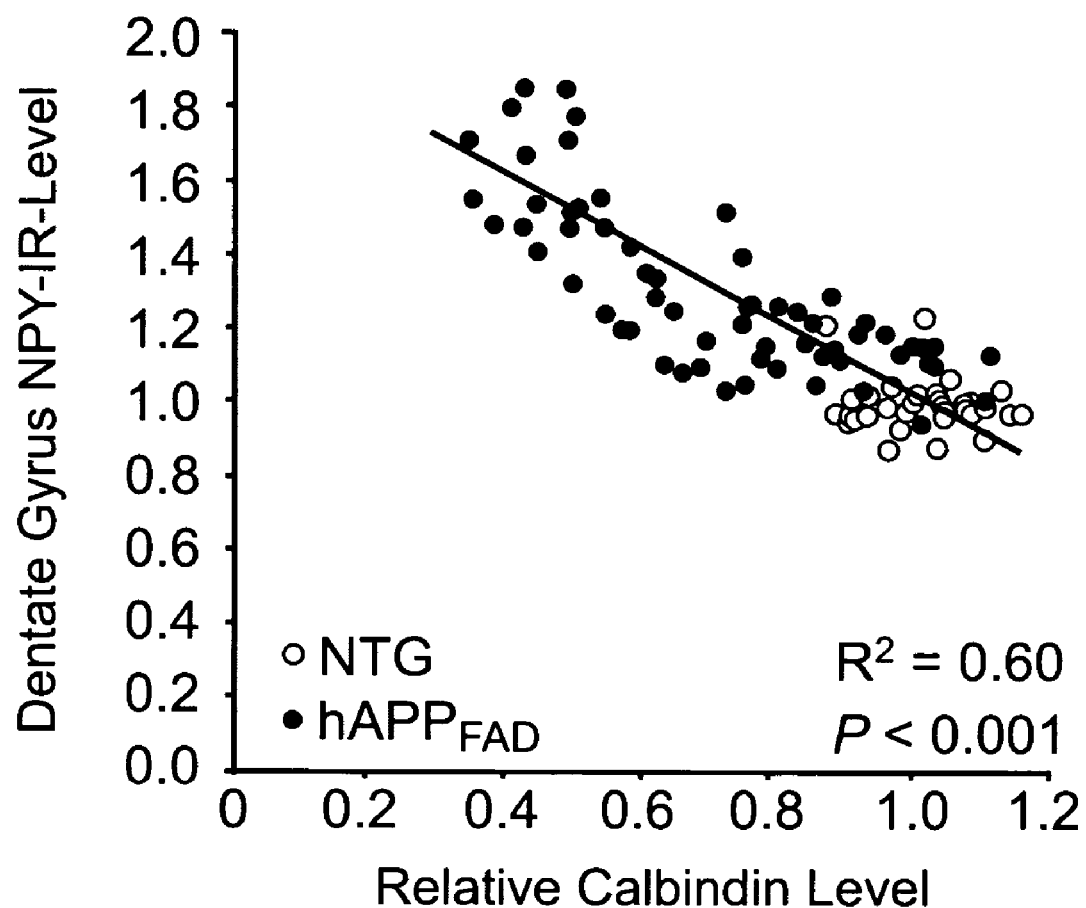
FIG. 5 depicts the observation that aberrant NPY/GABAergic sprouting in the molecular layer correlates with calbindin reduction (NTG; non-transgenic).
Figure 6:
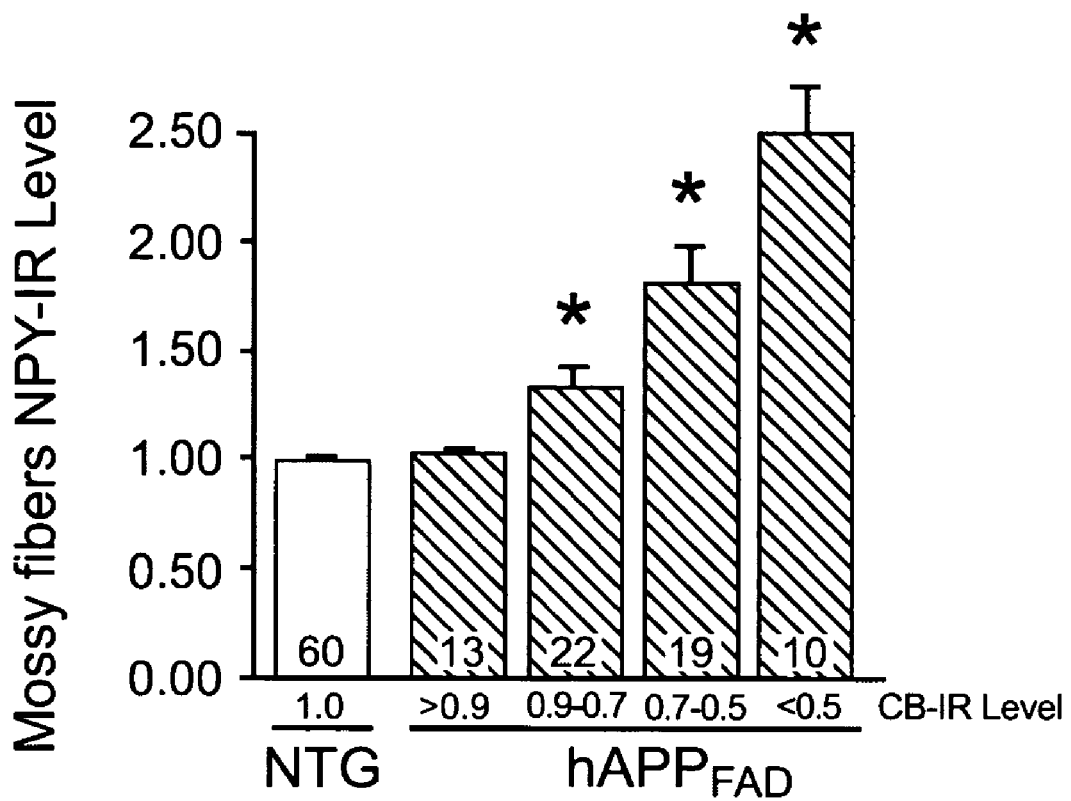
FIG. 6 depicts ectopic expression of NPY in mossy fibers in hAPP$_{FAD}$ mice.
Figure 7:
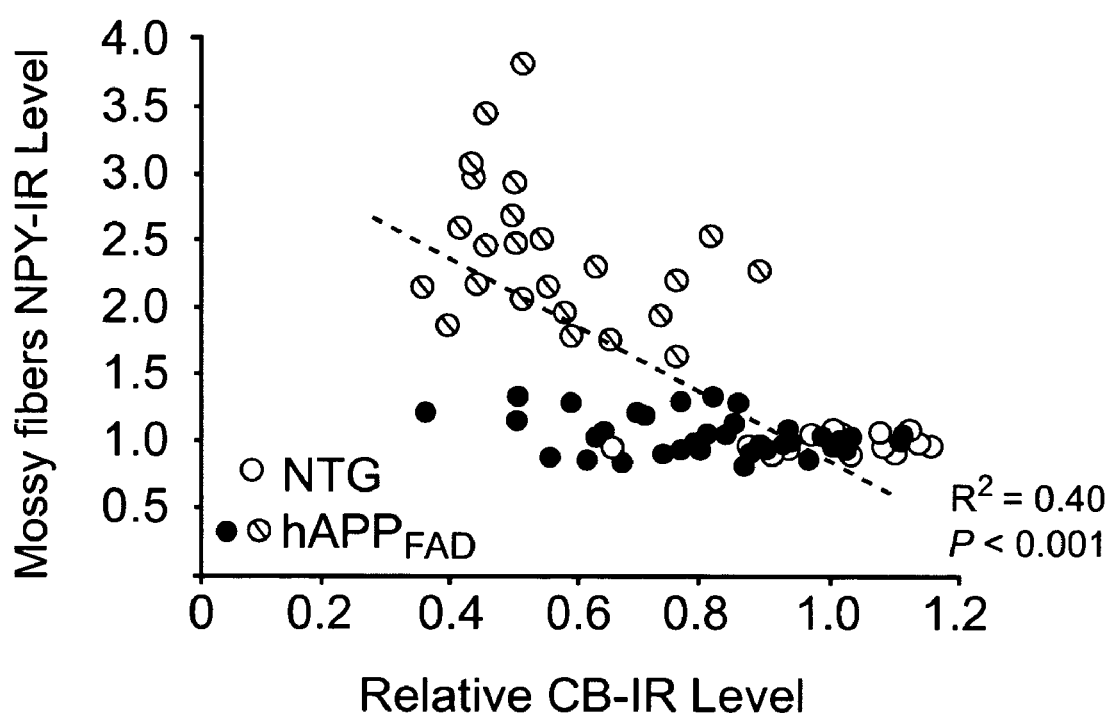
FIG. 7 depicts the observation that ectopic NPY expression in mossy fibers correlates with calbindin reductions.
Figure 8:
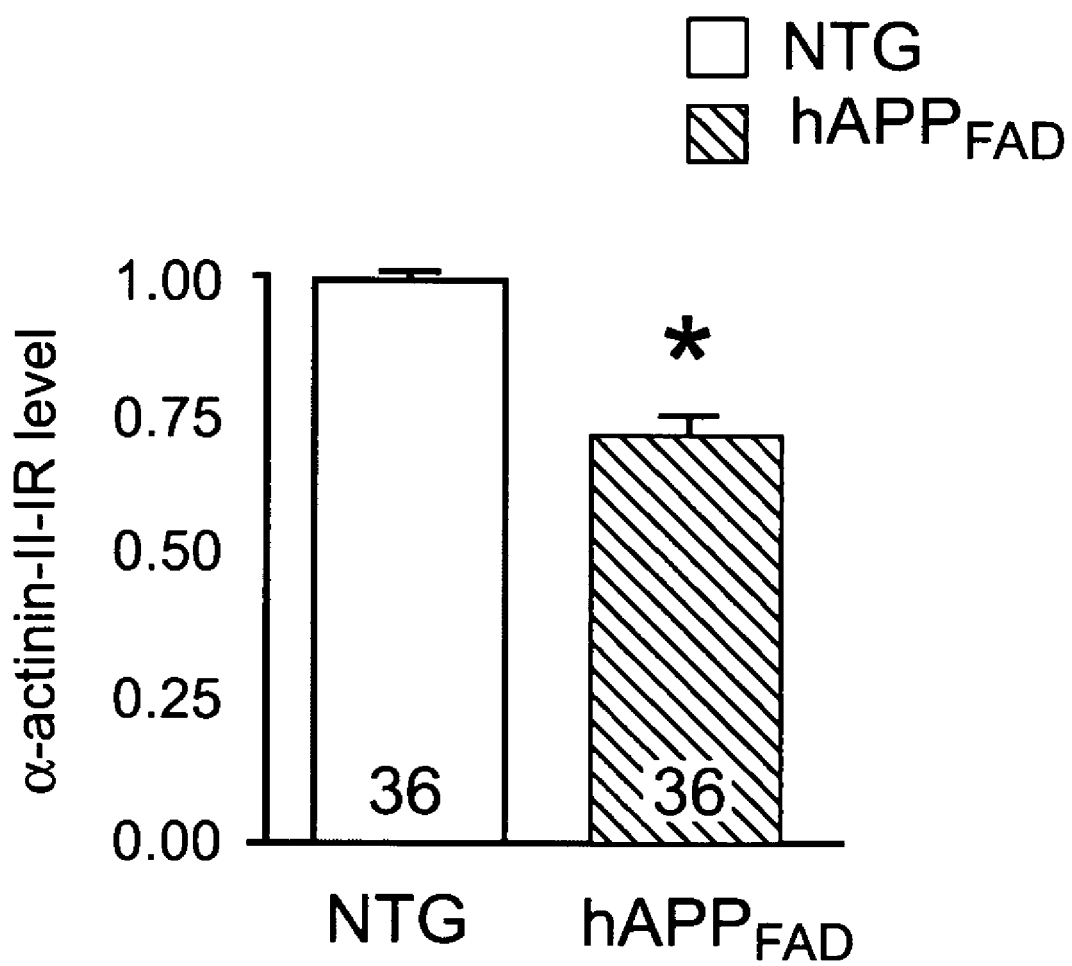
FIG. 8 depicts the observation that α-actinin-II is markedly reduced in the molecular layer of hAPP$_{FAD}$ mice.
Figure 9:
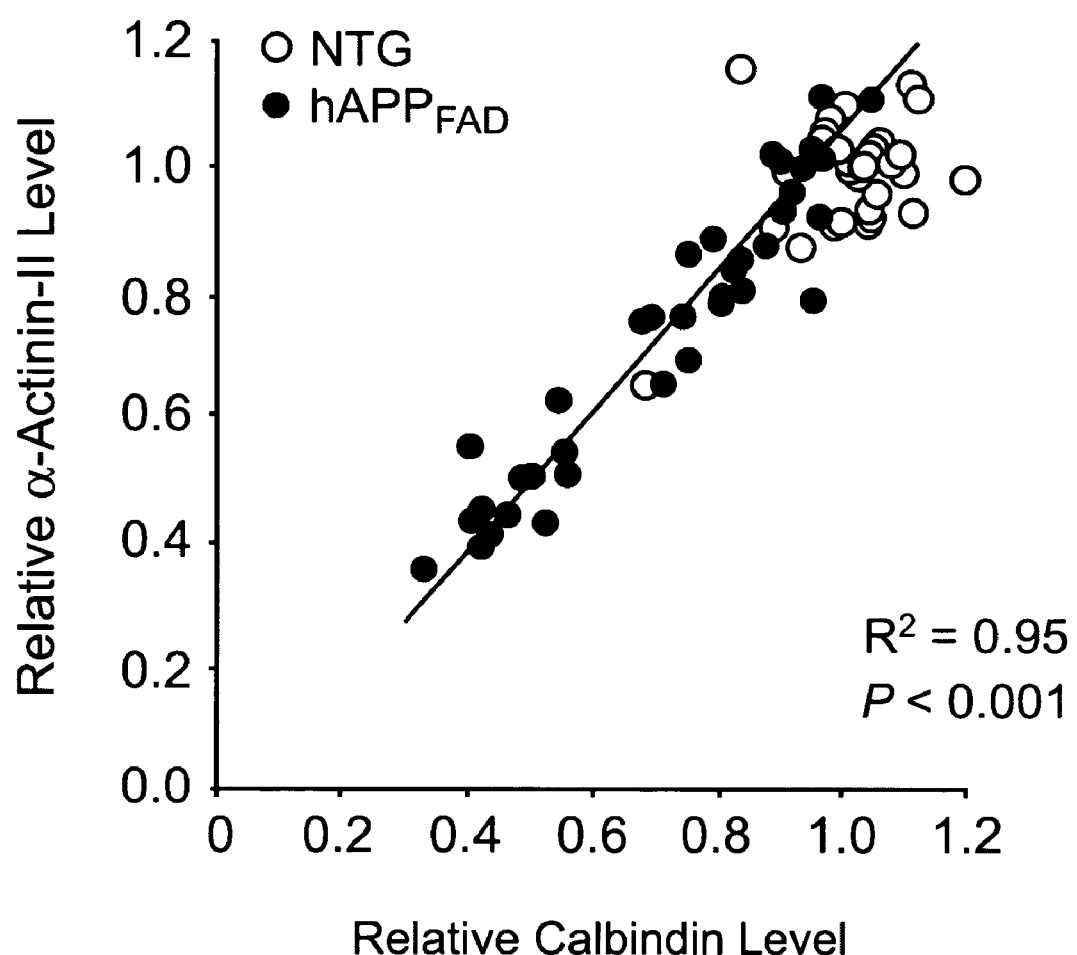
FIG. 9 depicts the observation that loss of α-actinin-II correlates with calbindin reductions in hAPP$_{FAD}$ mice.

FIGS. 4-10 present evidence of altered levels of other calcium-dependent proteins in animal models of amyloid-related pathologies. FIG. 4 depicts ectopic expression of NPY in mossy fibers, and aberrant NPY/GABAergic sprouting in the molecular layer in hAPP$_{FAD}$ mice. FIG. 5 depicts the observation that aberrant NPY/GABAergic sprouting in the molecular layer correlates with calbindin reduction (NTG; non-transgenic). FIG. 6 depicts ectopic expression of NPY in mossy fibers in hAPP$_{FAD}$ mice. FIG. 7 depicts the observation that ectopic NPY expression in mossy fibers correlates with calbindin reductions. FIG. 8 depicts the observation that α-actinin-II is markedly reduced in the molecular layer of hAPP$_{FAD}$ mice. FIG. 9 depicts the observation that loss of α-actinin-II correlates with calbindin reductions in hAPP$_{FAD}$ mice. FIG. 10 depicts the correlation of reductions in calbindin immunoreactivity (IR) with reductions in calbindin protein and mRNA in hAPP$_{FAD}$ mice.

Our findings that hAPP$_{FAD}$/Aβ is sufficient to reduce neuronal calbindin and c-Fos levels in vivo and that this effect is tightly associated with behavioral deficits has practical implications, particularly in light of increasing efforts to assess novel therapies for AD in transgenic mouse models. The behavioral testing of mice is time consuming, and test results obtained in different laboratories can vary widely. Crabbe, J. C., Wahlsten, D. & Dudek, B. C. Genetics of mouse behavior: Interactions with laboratory environment. *Science* 284, 1670-1672 (1999). Reliable molecular indicators of behavioral deficits circumvent these obstacles and facilitate the preclinical assessment of AD treatments.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting an amyloid peptide-related neurological disorder in a transgenic mouse model of the disorder, the method comprising:

detecting a level of a calcium-responsive gene product in hippocampal tissue of the transgenic mouse model, wherein the calcium-responsive gene product is selected from a calbindin polypeptide, a neuropeptide Y polypeptide, an α-actinin II polypeptide, a Fos polypeptide, an Arc polypeptide, a phospho-ERK polypeptide, a calbindin mRNA, a neuropeptide Y mRNA, an α-actinin II mRNA, and a Fos mRNA, an Arc mRNA, and an ERK mRNA, and wherein the genome of said transgenic mouse comprises a transgene encoding a mutant amyloid precursor protein;

wherein detection of a level of calcium-responsive gene product in the hippocampal tissue that differs from a level of the calcium-responsive gene product associated with a normal control mouse is indicative of an amyloid peptide-related neurological disorder in the mouse.

2. The method of claim 1, wherein the transgenic mouse model is an hAPP$_{FAD}$/Aβ transgenic mouse model of Alzheimer's Disease.

3. The method of claim 1, wherein the hippocampal tissue is dentate gyrus.

4. The method of claim 1, wherein the neurological disorder is impaired spatial learning or impaired memory.

5. A method for identifying a candidate agent for treating an amyloid peptide-related neurological disorder, the method comprising:
   administering a test agent to a transgenic mouse model of an amyloid peptide-related neurological disorder, wherein the genome of said transgenic mouse comprises a transgene encoding a mutant amyloid precursor protein; and
   detecting a level of a calcium-responsive gene product in vitro in hippocampal tissue of the mouse, wherein the calcium-responsive gene product is selected from a calbindin polypeptide, a neuropeptide Y polypeptide, an α-actinin II polypeptide, a Fos polypeptide, an Arc polypeptide, a phospho-ERK polypeptide, a calbindin mRNA, a neuropeptide Y mRNA, an α-actinin II mRNA, and a Fos mRNA, an Arc mRNA, and an ERK mRNA;
   wherein detection of a level of calcium-responsive gene product in the hippocampal tissue that differs significantly from a level of the calcium-responsive gene product in the absence of the agent indicates that the test agent is a candidate agent for treating an amyloid peptide-related neurological disorder.

6. The method of claim 5, wherein the transgenic mouse model is an hAPP$_{FAD}$/Aβ transgenic mouse model of Alzheimer's disease.

7. The method of claim 5, wherein the hippocampal tissue is dentate gyrus.

8. The method of claim 5, wherein the neurological disorder is impaired spatial learning or impaired memory.

9. The method of claim 1, wherein the amyloid peptide-related neurological disorder is a behavioral deficit.

10. The method of claim 5, wherein the amyloid peptide-related neurological disorder is a behavioral deficit.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
ggaaaggagc tgcagaactt gat                                    23

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
ttccggtgat agctccaatc c                                      21

<210> SEQ ID NO 3
<211> LENGTH: 25
<212> TYPE: DNA
<213> ORGANISM: Artificial Sequence

```
<220> FEATURE:
<223> OTHER INFORMATION: primer

<400> SEQUENCE: 3
aacctggtgc tggattgtat ctagt                                         25

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
ttcttagttt aatattggtc gtttctaatt g                                  31

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gggaagccca tcaccatctt                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gccttctcca tggtggtgaa                                               20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gaggaggatg actcggatgt ct                                            22

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
agccacttct tcctcctctg cta                                           23
```